US005524057A

United States Patent [19]

Akiho et al.

[11] Patent Number: 5,524,057

[45] Date of Patent: Jun. 4, 1996

[54] NOISE-CANCELING APPARATUS

[75] Inventors: Masaichi Akiho; Nozomu Saito; Tatsuo Owaki, all of Iwaki; Kunio Miyauchi; Akira Suto, both of Wako, all of Japan

[73] Assignees: Alpine Electronics Inc., Japan; Honda Giken Kogyo Kabushiki Kaisha, Japan

[21] Appl. No.: 72,969

[22] Filed: Jun. 8, 1993

[30] Foreign Application Priority Data

Jun. 19, 1992 [JP] Japan .................................... 4-161154
Jul. 8, 1992 [JP] Japan .................................... 4-180811

[51] Int. Cl.[6] .................................................. A61F 11/06

[52] U.S. Cl. .................................................................. 381/71

[58] Field of Search ........................................ 381/71, 94

[56] References Cited

U.S. PATENT DOCUMENTS 4,480,333 10/1984 Ross ........................................ 381/71
4,637,048 1/1987 Swinbanks ................................ 381/71

OTHER PUBLICATIONS

Dorf, Richard C., Modern Control Systems, 1974, Second edition, p. 47.

*Primary Examiner*—Forester W. Isen
*Assistant Examiner*—Ping W. Lee
*Attorney, Agent, or Firm*—Staas & Halsey

[57] ABSTRACT

A noise-canceling apparatus includes a canceling-sound generating source for outputting a canceling sound, a sensor for sensing a composite sound that is a composite of noise and the canceling sound at a noise-canceling point, a noise-canceling controller, to which a composite-sound signal and a reference signal conforming to noise generated by a noise source are inputted, for generating a noise-canceling signal by executing adaptive signal processing so as to cancel out the noise at the noise-canceling point using these signals and inputting the noise-canceling signal to the canceling-sound generating source, and a frequency-characteristic correcting unit provided on the input side of an adaptive filter, which constructs the noise-canceling controller, and having a frequency characteristic that is substantially symmetrical, about a 0 dB line, with respect to the frequency characteristic of a canceling-sound propagation system. The noise-canceling controller executes adaptive signal processing with a signal obtained by inputting the reference signal to the frequency-characteristic correcting unit being adopted as a true reference signal.

4 Claims, 19 Drawing Sheets

NOISE-CANCELING APPARATUS

BACKGROUND OF THE INVENTION

This invention relates to a noise-canceling apparatus and, more particularly, to a noise-canceling apparatus capable of canceling noise at a prescribed position (observation point) in an automotive vehicle so that pleasant audio can be heard.

A known method of dealing with noise involves using a sound-absorbing material (this is a method of passive control). With a method that relies upon use of a sound-absorbing material, however, forming a silent area of little noise is troublesome and low-pitched sounds are not eliminated effectively. In particular, when noise within the passenger compartment of an automotive vehicle is prevented by passive control, the vehicle is increased in weight and the elimination of noise cannot be performed effectively.

For this reason, active-control methods in which a noise-canceling sound whose phase is the opposite of the noise is emitted from a speaker so as to reduce the noise have become the focus of attention and these methods are being put into practical use in factory and office interiors. Systems for reducing noise by active control have been proposed for the passenger compartments of automotive vehicles as well.

FIG. 9 is a block diagram of an apparatus for achieving the cancellation of sound. As shown in FIG. 9, an engine 11 which is a source of noise has its rotational speed R sensed by an rpm sensor 12. The output R of the sensor 12 is applied to a reference-signal generator 13, which generates a sinusoidal signal having a fixed amplitude and a frequency that conforms to the rotational speed R of the engine 11. The sinusoidal signal serves as a reference signal $x_n$. When an engine is a source of noise, the noise generated by rotation of the engine has periodicity (this is periodic noise) and the frequency of the noise is dependent upon the engine rotational speed. In the case of a four-cylinder engine, for example, the frequency of periodic noise generated within the passenger compartment is 20 Hz when the rotational speed is 600 rpm (=10 rps) and 200 Hz when the rotational speed is 6000 rpm (=100 rps). These are secondary harmonics of the engine speed. Accordingly, the reference-signal generator 13 stores the sinusoidal data in a ROM and generates the reference signal $x_n$ by reading out and delivering this data as necessary. The timing at which this data is read out and delivered is controlled in accordance with the engine rotational speed R so that the reference signal outputted will have a frequency conforming to the engine rotational speed R.

The reference signal $x_n$ generated by the reference-signal generator 13 is applied to a noise-canceling controller 14 as an input. Also fed into the controller 14 is an error signal $e_n$, which is a composite-sound signal that is a synthesis of noise $S_n$ and a noise-canceling sound $S_c$ at a noise-canceling position (an observation point, such as a point in the vicinity of the ears of the driver) within the passenger compartment. The noise-canceling controller 14 outputs a noise-canceling signal $N_c$ by executing adaptive signal processing so as to minimize the error signal $e_n$. The controller 14 includes an adaptive signal processor 14*a*, an adaptive filter 14*b* constructed as a digital filter, a DA converter 14*c* for converting the output of the adaptive filter 14*b* into the noise-canceling signal $N_c$, which is an analog quantity, and a filter 14*d* for producing a filtered-X signal (a reference signal $r_n$ for signal processing) by superimposing, on the reference signal $x_n$, the propagation characteristic of a canceling-sound propagation system (secondary-sound propagation system) 18 extending from a speaker to the noise-canceling point.

A power amplifier 15 amplifies the noise-canceling signal $N_c$ and applies the amplified signal to a canceling speaker 16, which emits the noise-canceling sound $S_c$. An error microphone 17 is disposed at the noise-canceling point so as to detect the aforesaid composite-sound signal, which is a synthesis of the noise $S_n$ and the noise-canceling sound $S_c$, and output a composite-sound signal as the error signal $e_n$.

The error signal $e_n$ at the noise-canceling point and the filtered-X signal $r_n$, which is produced by the filter 14*d*, enter the adaptive signal processor 14*a*, which decides the coefficients of the adaptive filter 14*b* by using these two signals to execute adaptive signal processing in such a manner that the noise at the noise-canceling point is canceled out. For example, the adaptive signal processor 14*a* decides the coefficients of the adaptive filter 14*b* in accordance with a well-known filtered-X LMS (least mean square) algorithm so as to minimize the error signal en that has entered from the error microphone 17. In accordance with the coefficients decided by the adaptive signal processor 14*a*, the adaptive filter 14*b* subjects the reference signal $x_n$ to digital filtering processing so that the DA converter 14*c* will deliver the sound-canceling signal $N_c$. It should be noted that the reference signal $x_n$ must be a signal having a high correlation with respect to the noise $S_c$ to be canceled; sounds having no correlation with the reference signal are not canceled out.

When the engine 11 rotates, its rotational speed R is sensed by the rpm sensor 12, the reference-signal generator 13 generates the reference signal $x_n$ [see (a) in FIG. 10], whose frequency conforms to the engine rotational speed R, and the reference signal $x_n$ enters the noise-canceling controller 14. At this time the periodic engine sound (periodic noise) generated by the engine 11 reaches the noise-canceling point upon propagating through space having a noise propagating system (a primary-noise propagating system) that exhibits a prescribed transfer function. Accordingly, the noise (engine sound) $S_n$ at the noise-canceling point has a slightly lower level and a slight delay, as illustrated at (b) in FIG. 10.

Initially, the noise-canceling controller 14 produces the noise-canceling signal $N_c$ so as to have a phase opposite that of the reference signal $x_n$, as a result of which the canceling speaker 16 outputs the canceling sound $S_c$ shown at (c) in FIG. 10, by way of example. However, since the level and phase of the noise $S_n$ are displaced somewhat from the level and phase of the canceling sound $S_c$, the noise is not canceled out by the canceling sound $S_c$ and, hence, the error signal en is generated. The noise-canceling controller 14 decides the coefficients of the adaptive filter 14*b* by performing adaptive signal processing in such a manner that the error signal $e_n$ is minimized. In an ideal case, the phase of the canceling sound $S_c$ will be opposite that of the noise $S_n$ and the levels thereof will be in agreement, as shown at (d) in FIG. 10, so that the noise is canceled out.

In order simplify the description, the foregoing example deals with one noise source, one source (the speaker) for generating the canceling sound, and one noise-canceling point (the observation point). In actuality, however, there is more than one noise source and more than point (observation point) at which noise is desired to be canceled. In such case, more than one speaker is necessary since noise at a plurality of points cannot be canceled with only one speaker. FIG. 11 is a block diagram of a conventional noise-canceling apparatus for a case in which there are K-number of noise sources, M-number of speakers and L-number of observation points.

Numeral 21 denotes a noise-canceling controller (which corresponds to the noise-canceling controller 14 in FIG. 9) that operates so as to cancel out noise at each of a number of observation points. Numeral 22 denotes a primary-sound hypothetical propagation system (noise propagation system), which expresses systems along which noise is propagated from each noise source (not shown) to each observation point. Numeral 23 represents a secondary-sound propagation system (noise-canceling sound propagation system), which expresses systems along which canceling sound is propagated from each speaker to each observation point. The system 23 includes the characteristics of the speakers (not shown). Numeral 24 designates a signal synthesizer, which implements the function of a microphone at each observation point. The signal synthesizer 24 includes adders $24_1$~$24_1'$ corresponding to a microphone at a first observation point, adders $24_2$~$24_2'$ corresponding to a microphone at a second observation point, . . . , and adders $24_L$~$24_L'$ corresponding to a microphone at an L-th observation point. Further, $d_{d1n}$~$d_{dLn}$ represent external noise that is not the object of cancellation at each of the observation points.

The noise-canceling controller 21 includes a multiple-input/multiple-output adaptive filter (hereinafter referred to simply as an adaptive filter) 21*a* for inputting noise-canceling signals $y_{a1n}$~$y_{aMn}$ to the speakers upon being provided with inputs of reference signals $x_{a1n}$~$x_{aKn}$ (outputted by a reference-signal generator, not shown) conforming to the noise components generated by the noise sources, a filtered-X signal producing filter 21*b*, which is fabricated using the elements (propagation elements) of a transfer-function matrix of the secondary-sound propagation system 23, this filter being provided with inputs of the reference signals $x_{a1n}$~$x_{aKn}$ conforming to the noise generated by the noise sources, and an adaptive signal processor 21*c*, which is provided with inputs of error signals $e_{1n}$~$e_{Ln}$ prevailing at the observation points and filtered-X signals $r_{111n}$~$r_{LMKn}$ outputted by the filter 21*b*, for deciding the coefficients of the adaptive filter 21*a* by executing adaptive signal processing using these input signals so as to cancel out the noise at each observation point.

FIGS. 12A and 12B are diagrams for describing the primary-sound hypothetical propagation system 22. The noise generated by K-number of noise sources $N_{G1}$~$NG_K$ reaches microphones ($MIC_1$~$MIC_L$), which are provided at the respective observation points, upon propagating through the primary-sound propagation system 22 having prescribed frequency and phase characteristics. Accordingly, if we let $H_{ji}$ represent the transfer characteristic of a propagation system in which noise from an i-th noise source $NG_i$ reaches a j-th microphone $MIC_j$, the primary-noise hypothetical propagation system 22 will be expressed as shown in FIG. 12B and the transfer-function matrix (H) thereof will be as follows:

$$(H) = \begin{bmatrix} H_{11}H_{12}H_{13}\ldots H_{1K} \\ H_{21}H_{22}H_{23}\ldots H_{2K} \\ \cdot \\ \cdot \\ H_{L1}H_{L2}H_{L3}\ldots H_{LK} \end{bmatrix}$$

Each element $H_{ij}$ of the transfer-function matrix (H) is implemented by a FIR-type digital filter shown in FIG. 13. More specifically, each element is realized by a digital filter comprising delay elements DL for successively delaying the input signal by one sampling period, multipliers ML for multiplying the outputs of the delay elements by coefficients $h_0$, $h_1$, $h_2$, . . . , and adders AD for adding the outputs of the multipliers.

FIGS. 14A, 14B are views for describing the secondary-noise propagation system 23. As shown in FIG. 14A, noise-canceling sounds generated by speakers $SP_1$~$SP_M$ arrive at the microphones $MIC_1$~$MIC_L$, which are provided at the respective observation points, upon propagating through the secondary propagation system 23 having prescribed frequency and phase characteristics. Accordingly, if we let $C_{ji}$ represent the transfer characteristic of a secondary-noise propagation system in which a canceling sound based upon an i-th noise-canceling signal $y_{ain}$ reaches the j-th microphone $MIC_j$, the secondary-noise propagation system 23 will have the form of the model shown in FIG. 14B and the transfer-function matrix (C) thereof will be as follows:

$$(C) = \begin{bmatrix} C_{11}C_{12}C_{13}\ldots C_{1M} \\ C_{21}C_{22}C_{23}\ldots C_{2M} \\ \cdot \\ \cdot \\ C_{L1}C_{L2}C_{L3}\ldots C_{LM} \end{bmatrix}$$

Each element of the transfer-function matrix (C) is implemented by a FIR-type digital filter shown in FIG. 13, just as in the case of the primary-sound hypothetical propagation system 22. More specifically, each element is realized by a digital filter comprising delay elements DL for successively delaying the input signal by one sampling period, multipliers ML for multiplying the outputs of the delay elements by coefficients $c_0$, $c_1$, $c_2$, . . . , and adders AD for adding the outputs of the multipliers.

FIG. 15 is a block diagram showing the filtered-X signal-producing filter 21*b* fabricated using each element $C_{ij}$ of the transfer-function matrix (C) of the secondary-sound propagation system 23.

The adaptive signal processor 21*c* updates the coefficients of the adaptive filter 21*a* by executing adaptive signal processing based upon the reference signals $x_{a1n}$~$x_{aKn}$ and the signals $e_{1n}$~$e_{Ln}$ that are a composite of the noise and canceling sounds at each of the observation points, and the adaptive filter 21*a*, to which the reference signals $x_{a1n}$–$x_{aKn}$ are applied as inputs, generates the noise-canceling signals $y_{a1n}$~$y_{aMn}$ and applies these signals to the speakers to cancel out the sound at each observation point.

The noise-canceling signals $y_{a1n}$~$y_{aMn}$ outputted by the adaptive filter 21*a* do not reach the observation points as is. Rather, they reach the observation points upon being influenced by the frequency and phase characteristics of the secondary-sound propagation system 23. As a consequence, the adaptive signal processor 21*c* performs highly sophisticated noise-canceling control not by using the reference signals $x_{a1n}$~$x_{aKn}$ as is but by employing a filtered-X LMS (multiple-error filtered X LMS, referred to as an "MEFX LMS") algorithm, which uses signals obtained by impressing the characteristics of the secondary-sound propagation system 23 on the reference signals. In other words, on the basis of the filtered-X LMS algorithm, the adaptive signal processor 21*c* updates the coefficients of the adaptive filter 21*a* using signals $r_{111n}$~$r_{LMKn}$, which are result of filtering the reference signals $x_{a1n}$~$x_{aKn}$ by the filter 21*b*, and the composite-sound signals (error signals) $e_{1n}$~$e_{Ln}$ at the observation points.

In FIG. 15, $C_{ij}$ represents a FIR-type digital filter for realizing each element $C_{ij}$ (see FIG. 14) of the transfer-function matrix (C) in the secondary-sound propagation system 23. The filter 21*b* is adapted so as to output the filtered-X signals $r_{111n}$~$r_{LMKn}$ upon impressing all of the propagation elements upon each of the reference signals $x_{a1n}$~$x_{aKn}$ (i.e., passing each reference signals through filters corresponding to all of the propagation elements). More specifically, the propagation elements $C_{11}$~$C_{L1}$ from the first speaker to all of the observation points are made to act upon the reference signal $x_{a1n}$ to produce the filtered-X signals $r_{111n}$~$r_{L11n}$, the propagation elements $C_{12}$~$C_{L2}$ from the second speaker to all of the observation points are made to act upon the reference signal $x_{a1n}$ to produce the filtered-X signals $r_{121n}$~$r_{L21n}$, . . . , and the propagation elements $C_{1M}$~$C_{LM}$ from the M-th speaker to all of the observation points are made to act upon the reference signal $x_{a1n}$ to produce the filtered-X signals $r_{1M1n}$~$r_{LM1n}$. All of the propagation elements are made to act upon each of the reference signals $x_{a2n}$, $x_{a3n}$, . . . $x_{aKn}$ in a similar manner. This may be expressed as follows:

$$R_{11}=(r_{111n}, r_{211n}, \ldots r_{L11n})$$

$$R_{21}=(r_{121n}, r_{221n}, \ldots r_{L21n}) \ldots R_{M1}=(r_{1M1n}, r_{2M1n}, \ldots r_{LM1n}) \ldots R_{MK}=(r_{1MKn}, r_{2MKn}, \ldots r_{LMKn})$$

FIG. 16 is a block diagram showing the multiple-input/multiple-output adaptive filter 21*a*, which has a structure similar to that of the primary-sound hypothetical propagation system 22 or secondary-sound propagation system 23. FIR-type digital filters are shown at $A_{11n}$~$A_{MKn}$. By way of example, each of these filters may be realized by delay elements $DL_1$, $DL_2$ . . . for successively delaying the input signal by one sampling period, multipliers $ML_1$, $ML_2$, $ML_3$ . . . for multiplying each delay-element output by coefficients $a_0$, $a_1$, $a_2$ . . . , and adders $AD_1$, $AD_2$ . . . for adding the multiplier outputs. The number of delay stages is limited to two.

The noise-canceling signal $y_{a1n}$ inputted to the first speaker is obtained by inputting the reference signals $x_{a1n}$~$x_{aKn}$ to the digital filters $A_{11n}$~$A_{1Kn}$ and then adding, the noise-canceling signal $y_{a2n}$ inputted to the second speaker is obtained by inputting the reference signals $x_{a1n}$~$x_{aKn}$ to the digital filters $A_{21n}$~$A_{2Kn}$ and then adding, . . . , and the noise-canceling signal $y_{aMn}$ inputted to the M-th speaker is obtained by inputting the reference signals $x_{a1n}$~$x_{aKn}$ to the digital filters $A_{M1n}$~$A_{MKn}$ and then adding.

When each of the FIR-type digital filters $A_{11n}$~$A_{MKn}$ in the adaptive filter 21*a* is composed of three coefficients (two delay stages), the adaptive signal processor 21*c* decides the values of the coefficients by executing adaptive signal processing for each of the three coefficients of the FIR-type digital filters $A_{11n}$~$A_{MKn}$. That is, the adaptive signal processor decides coefficients $a_0$, $a_1$, $a_2$ by performing the following operation with regard to these coefficients $a_0$, $a_1$, $a_2$ of one FIR-type digital filter $A_{ijn}$:

$$\begin{bmatrix} a_0(n+1) \\ a_1(n+1) \\ a_2(n+1) \end{bmatrix} = \begin{bmatrix} a_0(n) \\ a_1(n) \\ a_2(n) \end{bmatrix} - \mu \begin{bmatrix} R_{ij}(n) \\ R_{ij}(n-1) \\ R_{ij}(n-1) \end{bmatrix} e_n \quad (1)$$

where $$\begin{aligned} R_{ij} &= x_{ajn}(C_i) \quad (2) \\ &= x_{ajn}(C_{ii}, C_{2i}, C_{3i}, \ldots, C_{Li}) \\ &= (r_{1ijn}, r_{2ijn}, \ldots, r_{Lijn}) \end{aligned}$$

-continued $$e_n = \begin{bmatrix} e_{1n} \\ e_{2n} \\ \cdot \\ \cdot \\ \cdot \\ e_{Ln} \end{bmatrix} \quad (3)$$

In Equation (1), (n) signifies the value at the present sampling time, (n–1) the value one sampling earlier, (n–1) the value two samplings earlier, and (n+1) the value from the present time to the next sampling time. Accordingly, $R_{ij}$(n–2) signifies the output of the filter 21*b* that conforms to the reference signal two samplings earlier, $R_{ij}$(n–1) signifies the output of the filter that conforms to the reference signal one sampling earlier, and $R_{ij}$ (n) signifies the output of the filter that conforms to the reference signal at the present time. Further, μ represents a constant (step-size parameter) of less than 1, and $e_n$ represents the signal (error signal) that is the composite of the noise and canceling sound at each of the L-number of observation points.

In accordance with this noise-canceling apparatus, the adaptive signal processor 21*c* decides the coefficients of the FIR-type digital filters $A_{11n}$~$A_{MKn}$, which constitute the adaptive filter 21*a*, by executing adaptive signal processing based upon the filtered-X signals $r_{111n}$~$r_{LMKn}$, which are outputted by the filter 21*b*, and the composite-sound signals (error signals) $e_{1n}$~$e_{Ln}$ that are a composite of the noise and canceling sounds at each of the observation points. The adaptive filter 21*a*, to which the reference signals $x_{a1n}$~$x_{aKn}$ are applied, generates the noise-canceling signals $y_{a1n}$~$y_{aMn}$ and applies these signals to the speakers $SP_1$~$SP_M$ (FIG. 14). Each speaker generates a canceling sound to cancel out the noise at each observation point.

FIG. 17 is a block diagram illustrating the details of the conventional noise-canceling apparatus for a case in which there are one noise source (K=1), two speakers (M=2) and two observation points, i.e., two microphones (L=2). Numeral 21*a* denotes the adaptive filter, which is composed of two FIR-type digital filters $A_{11n}$, $A_{21n}$, numeral 21*b* denotes the filtered-X signal producing filter, which is obtained by using digital filters to construct each of the propagation elements $C_{11}$, $C_{21}$, $C_{12}$, $C_{22}$ of the transfer-function matrix of the secondary propagation system, numerals 21*c*-1, 21*c*-2 denote adaptive signal processors (MEFX LMS) for deciding the coefficients of each of the digital filters in the adaptive filter 21*a*, $SP_1$, $SP_2$ represent speakers, and $MC_1$, $MC_2$ designate microphones disposed at the observation points.

FIG. 18 is a block diagram illustrating the details of the conventional noise-canceling apparatus for a case in which there are one noise source (K=1), four speakers (M=4) and four observation points, i.e., four microphones (L=4). Numeral 21*a* denotes the adaptive filter, which is composed of four FIR-type digital filters $A_{11n}$, $A_{21n}$, $A_{12n}$, $A_{22n}$, numeral 21*b* denotes the filtered-X signal producing filter, which is obtained by using digital filters to construct each of the propagation elements $C_{11}$, $C_{21}$, $C_{31}$, $C_{41}$ . . . , $C_{44}$ of the transfer-function matrix of the secondary propagation system, numerals 21*c*-1 through 21*c*-4 denote adaptive signal processors (MEFX LMS), $SP_1$~$SP_4$ represent speakers, and $MC_1$~$MC_4$ designate microphones disposed at the observation points.

The frequency characteristics, inclusive of the speaker characteristics, of the secondary propagation system from the speakers to each observation point are not flat but vary as a function of frequency. FIG. 19 is a characteristic diagram showing the characteristics of speaker frequency. A frequency characteristic up to a noise frequency of 200 Hz, which corresponds to an engine rotational speed of 6000 rpm (=100 rps), varies approximately linearly in conformity with frequency. The frequency characteristic of the secondary-sound propagation system 23, which is the result of adding the frequency characteristic within the passenger compartment to this speaker characteristic, varies in conformity with frequency.

If the frequency of the noise to be canceled is constant, the coefficient convergence characteristic of the adaptive filter that relies upon adaptive signal processing is improved so that the coefficient values of the adaptive filter quickly converge to their optimum values. As a result, a satisfactory noise-canceling effect is capable of being achieved.

However, the frequency of the noise to be canceled fluctuates from one moment to the next. For example, the engine frequency fluctuates from one moment to the next and in dependence upon vehicle velocity, and the frequency of the engine sound also varies. When the frequency of noise fluctuates, gain varies in accordance with the frequency characteristic of the secondary-sound propagation system 23, and the coefficient convergence characteristic of the adaptive filter that relies upon adaptive signal processing deteriorates (i.e., there is a decline in the follow-up capability). The result is that the noise-canceling effect cannot be manifested satisfactorily. More specifically, in the adaptive signal processor, processing for deciding adaptive filter coefficients that conform to the present frequency characteristic (gain) of the secondary-sound propagation system is executed. However, when the frequency characteristic (gain) fluctuates at the next point in time, the coefficients that have been decided do not take on appropriate values that conform to the frequency characteristic at this next point in time and the coefficients of the adaptive filter do not converge quickly. This causes a decline in the follow-up capability.

SUMMARY OF THE INVENTION

Accordingly, an object of the present invention is to provide a noise-canceling apparatus in which, even if the frequency of noise fluctuates so that there is a variation in the gain of the secondary-sound propagation system, the noise is canceled by applying compensation in such a manner that the gain is rendered constant.

Another object of the present invention is to provide a noise-canceling apparatus in which the effects of noise cancellation can be enhanced even if the frequency of noise fluctuates from one moment to the next.

A further object of the present invention is to provide a noise-canceling apparatus in which follow-up performance is improved so that the effects of noise cancellation can be enhanced.

According to the present invention, the foregoing objects are attained by providing a noise-canceling apparatus in which a frequency-characteristic correcting unit is provided on the input side of an adaptive filter and has a frequency characteristic that is approximately symmetrical with respect to the frequency characteristic of a canceling-sound propagation system about a 0 dB line. Adaptive signal processing is executed using a signal obtained by inputting a reference signal to the frequency-characteristic correcting unit as a true reference signal. More specifically, in accordance with the noise-canceling apparatus of the present invention, the overall frequency characteristic of the frequency-characteristic correcting unit and canceling-sound propagation system can be made substantially flat to improve the coefficient convergence of the adaptive filter that relies upon adaptive signal processing. This makes it possible to achieve a satisfactory noise-canceling effect.

Further, the foregoing objects are attained by providing a noise-canceling apparatus in which a frequency-characteristic correcting unit is provided either on the input side of a canceling-noise generating source or in a feedback section for feeding back a composite-sound signal (error signal) to a noise-canceling controller. The overall frequency characteristic of the frequency-characteristic correcting unit and canceling-sound propagation system is made substantially flat. In accordance with the noise-canceling apparatus of the invention, the overall frequency characteristic of the frequency-characteristic correcting unit and canceling-sound propagation system is made substantially flat to improve the coefficient convergence of the adaptive filter that relies upon adaptive signal processing. This makes it possible to achieve a satisfactory noise-canceling effect.

Other features and advantages of the present invention will be apparent from the following description taken in conjunction with the accompanying drawings.

DESCRIPTION OF THE PREFERRED EMBODIMENTS

(a) First embodiment of the invention

Overall configuration

Figure 1:
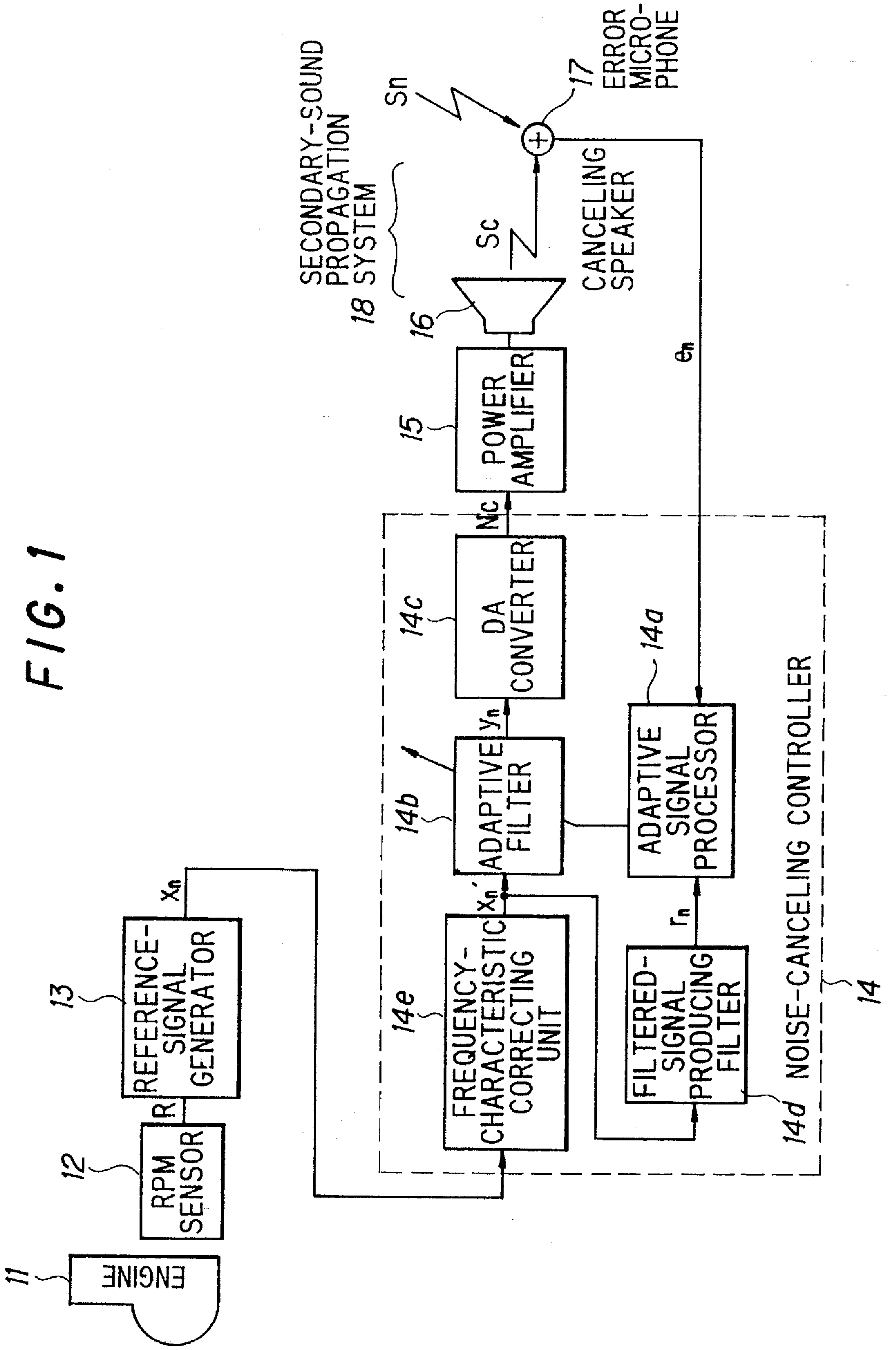
FIG. 1 is a block diagram showing a first embodiment of the present invention.
Figure 9:
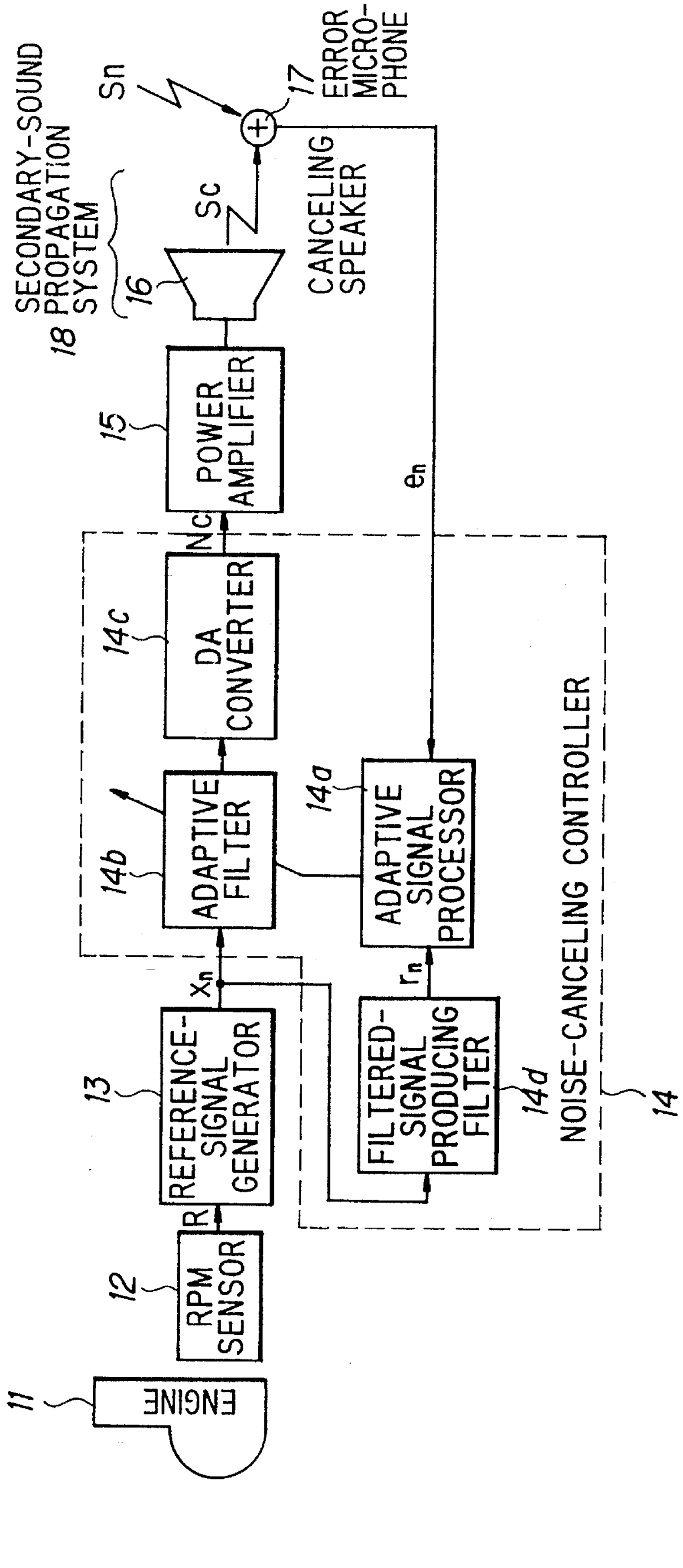
FIG. 9 (PRIOR ART)
FIG. 9 is a block diagram showing a noise-canceling apparatus according to the prior art.
Figure 10:
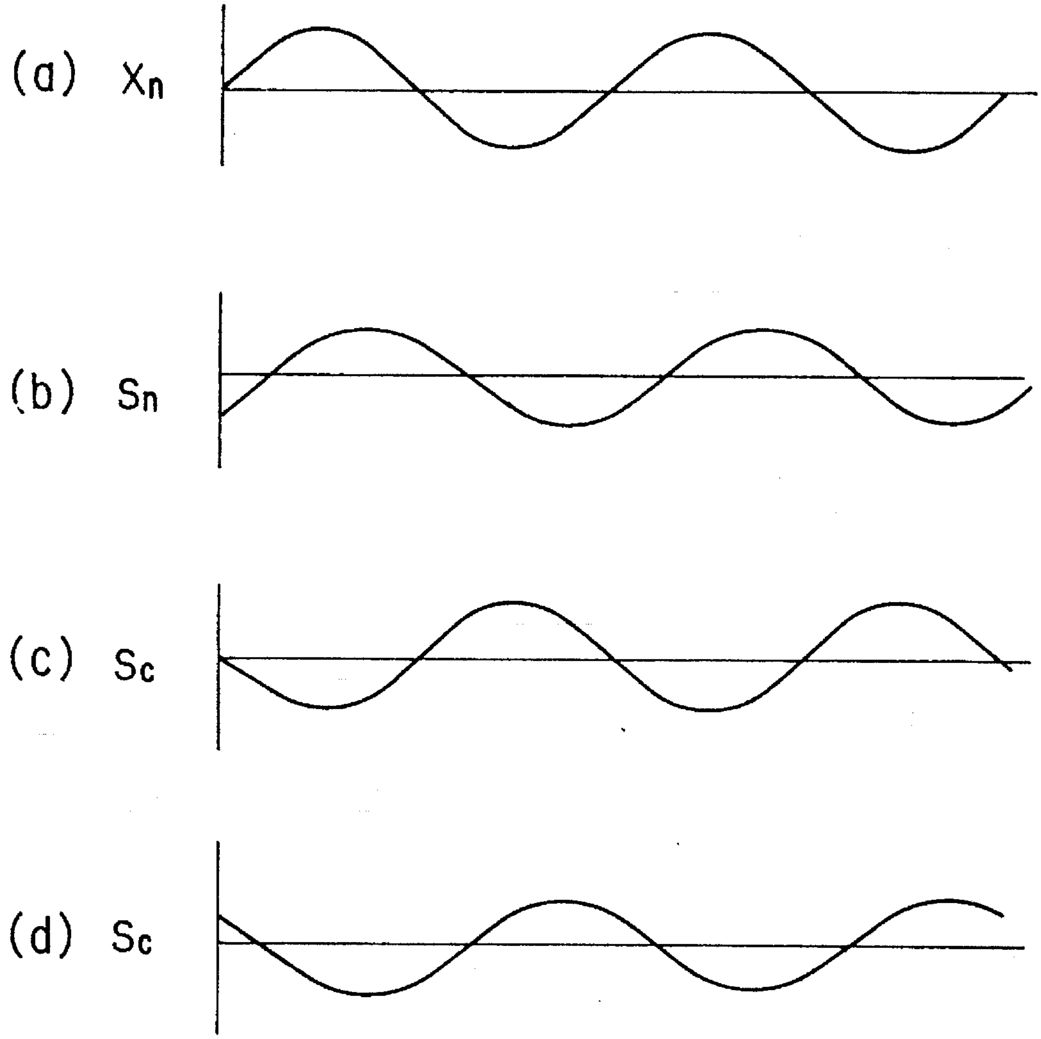
FIG. 10 (PRIOR ART)
FIG. 10 is a diagram of waveforms for describing a noise-canceling operation.
Figure 11:
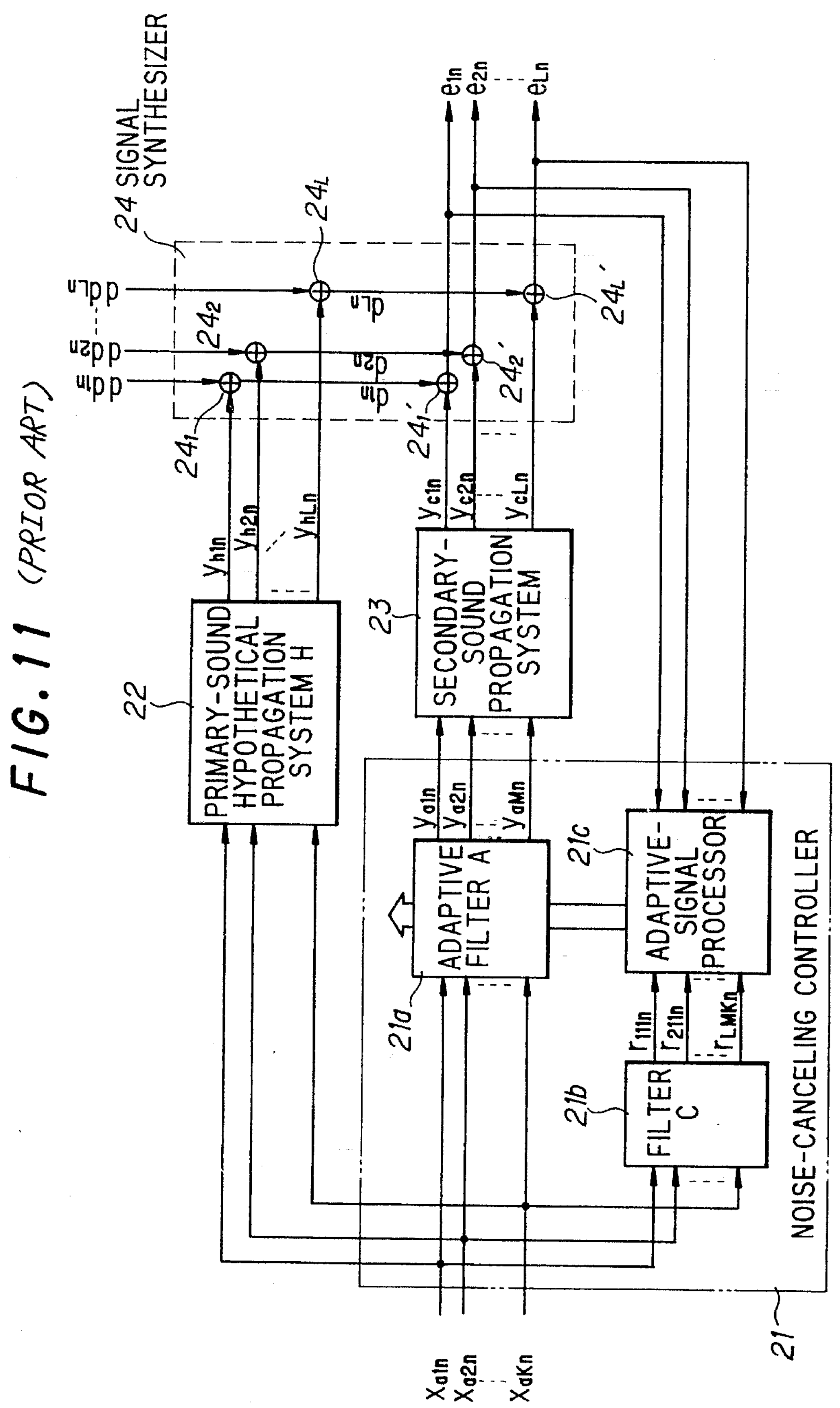
FIG. 11 (PRIOR ART)
FIG. 11 is a block diagram showing a prior-art noise-canceling apparatus for a case in which there are a plurality of noise sources, speakers and observation points.
Figure 12A:
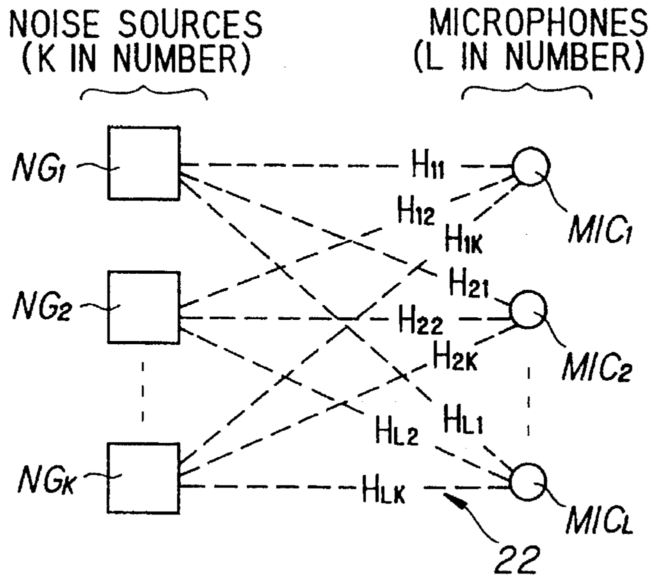
FIG. 12A (PRIOR ART)
FIG. 12A is an explanatory view of a primary-sound hypothetical propagation system.
Figure 12B:
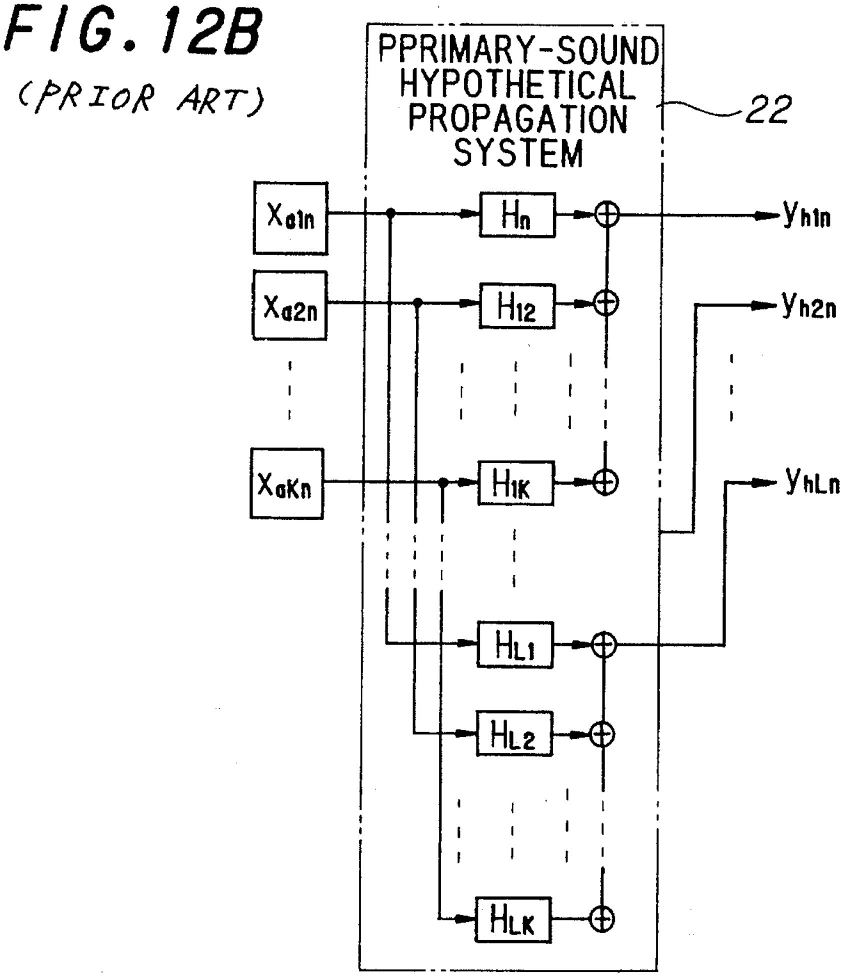
FIG. 12B (PRIOR ART)
FIG. 12B shows an example in which a primary-sound hypothetical propagation system is realized.
Figure 13:
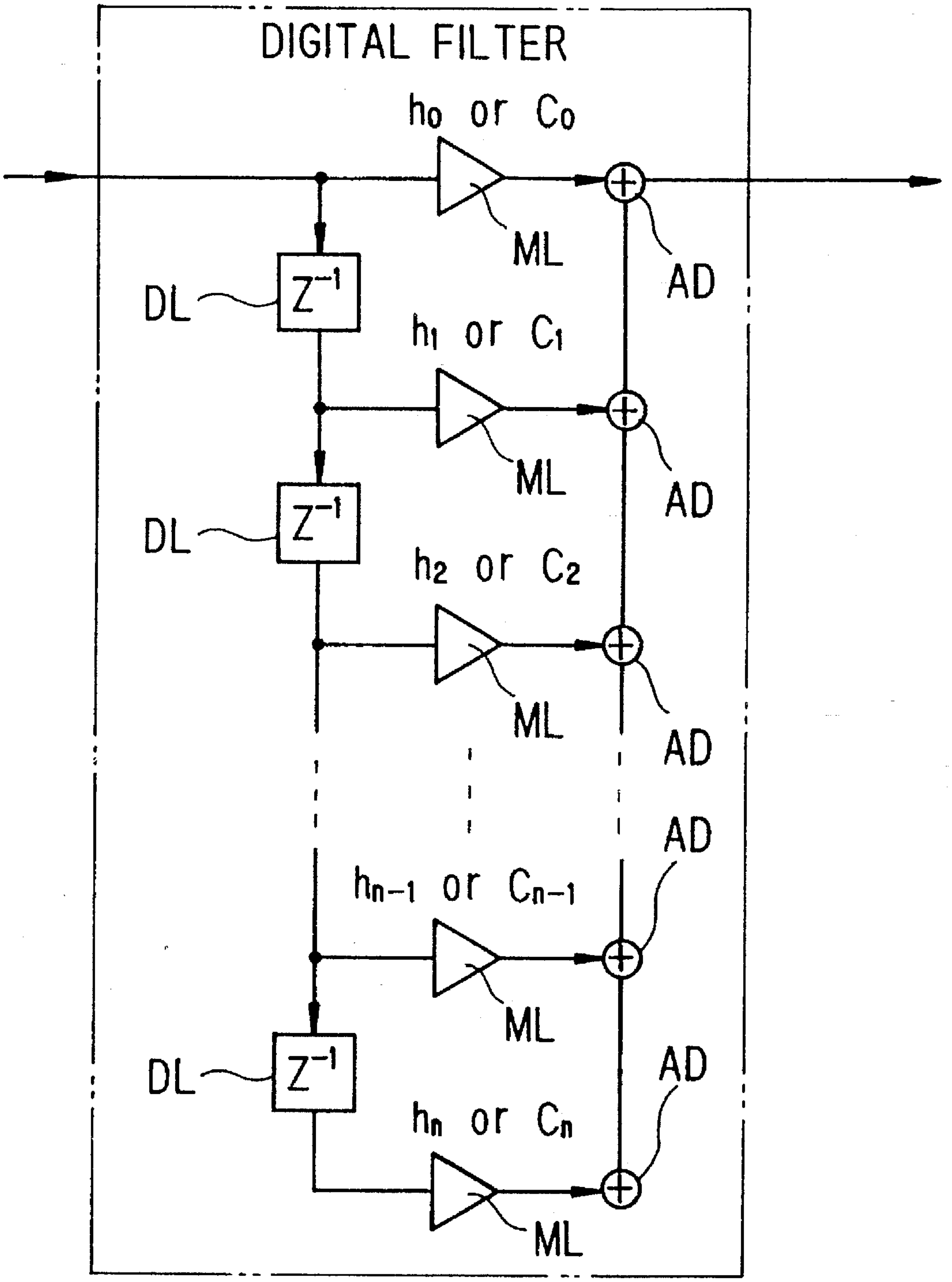
FIG. 13 (PRIOR ART)
FIG. 13 is a block diagram showing a digital filter for realizing each element of a transfer-function matrix.
Figure 14A:
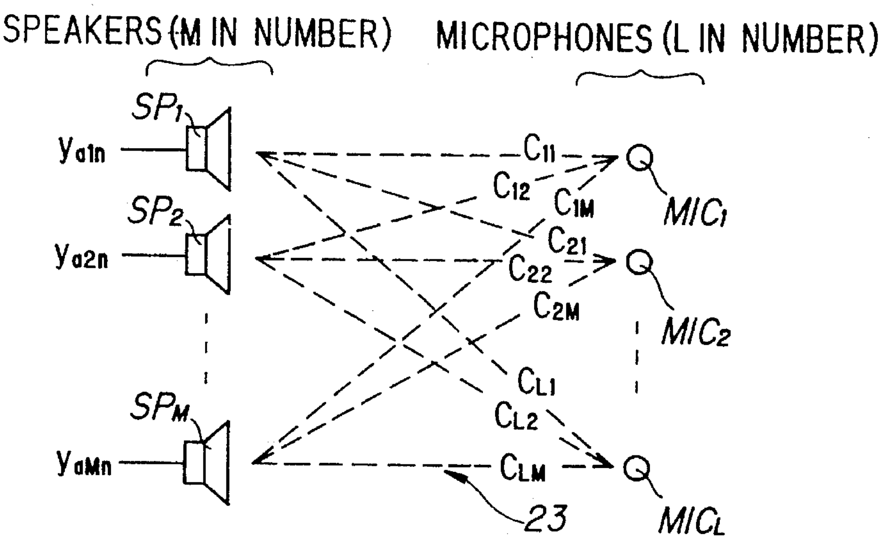
FIG. 14A (PRIOR ART)
FIG. 14A is an explanatory view of a secondary-sound propagation system.
Figure 14B:
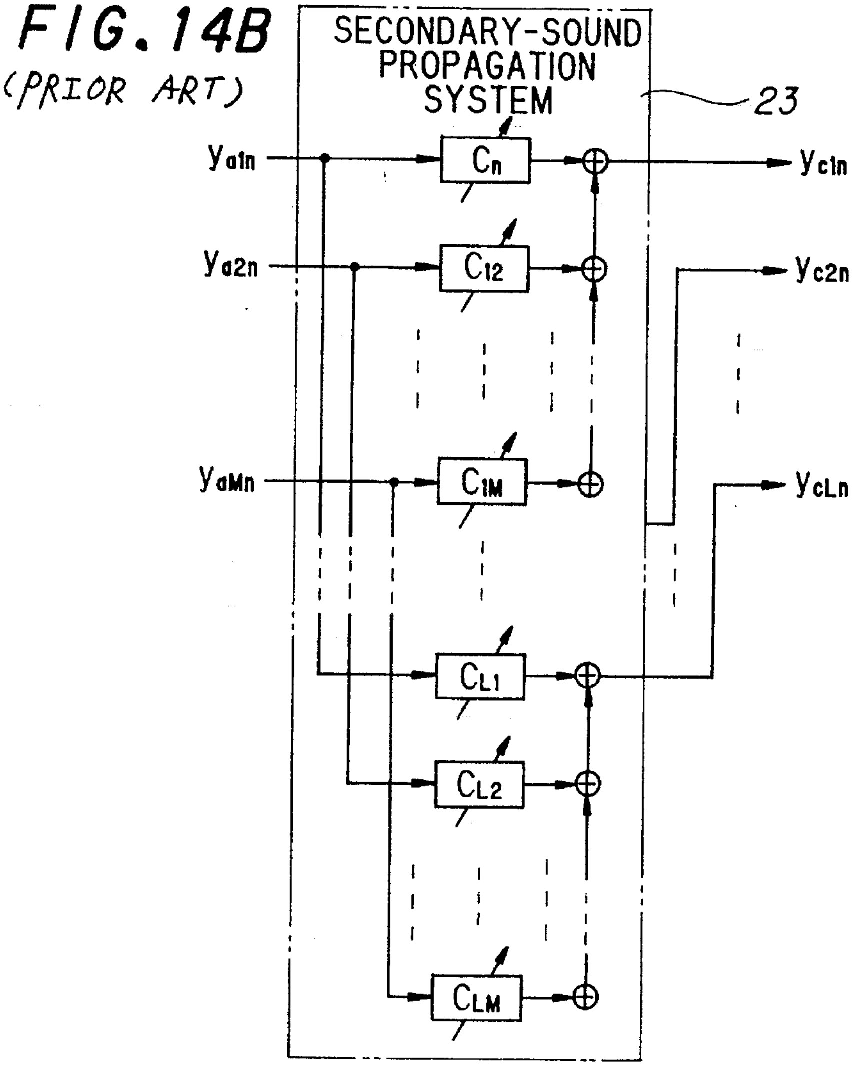
FIG. 14B (PRIOR ART)
FIG. 14B shows an example in which a secondary-sound propagation system is realized.
Figure 15:
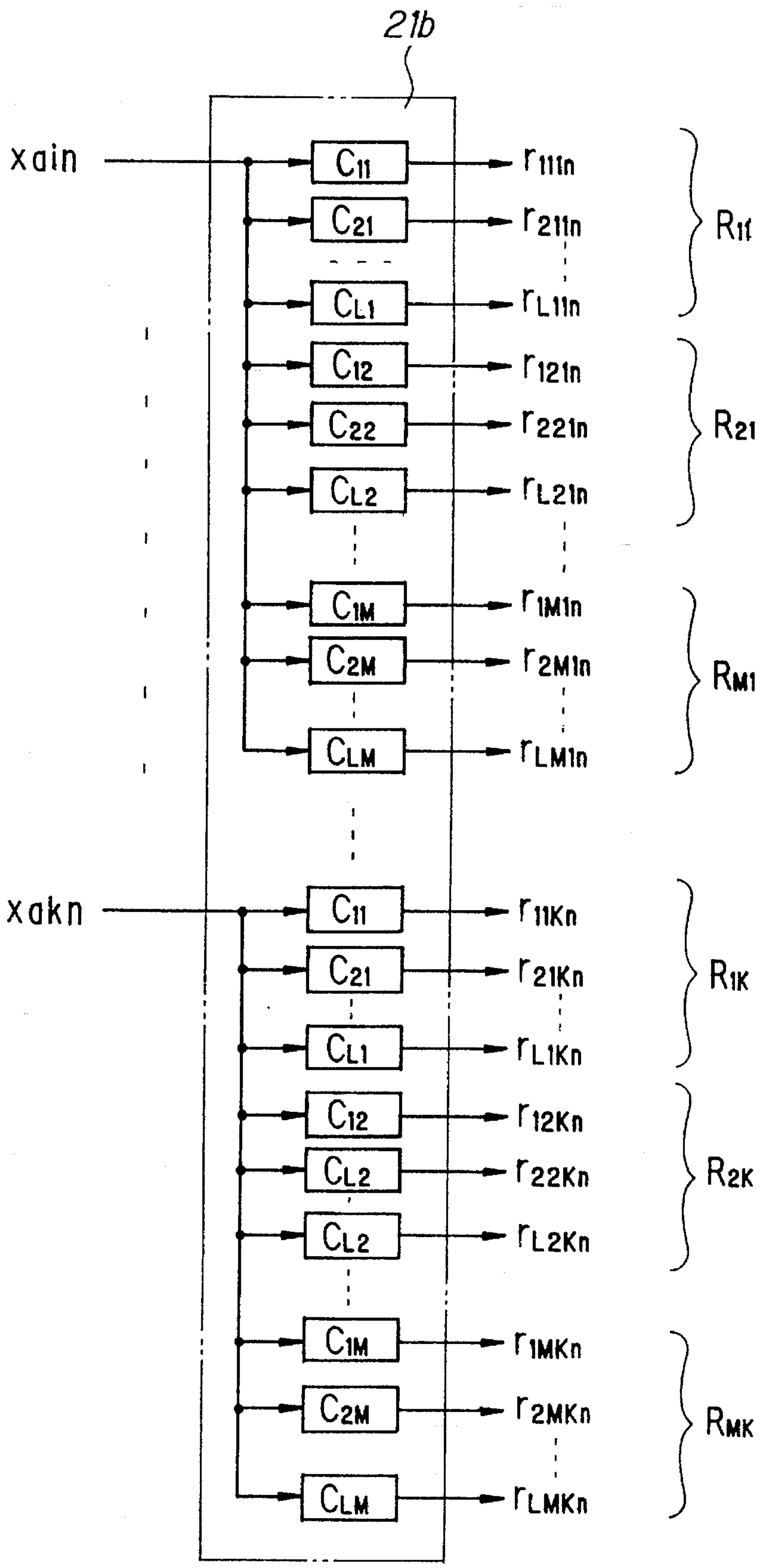
FIG. 15 (PRIOR ART)
FIG. 15 is a block diagram showing a filter for producing a filtered-X signal.
Figure 16:
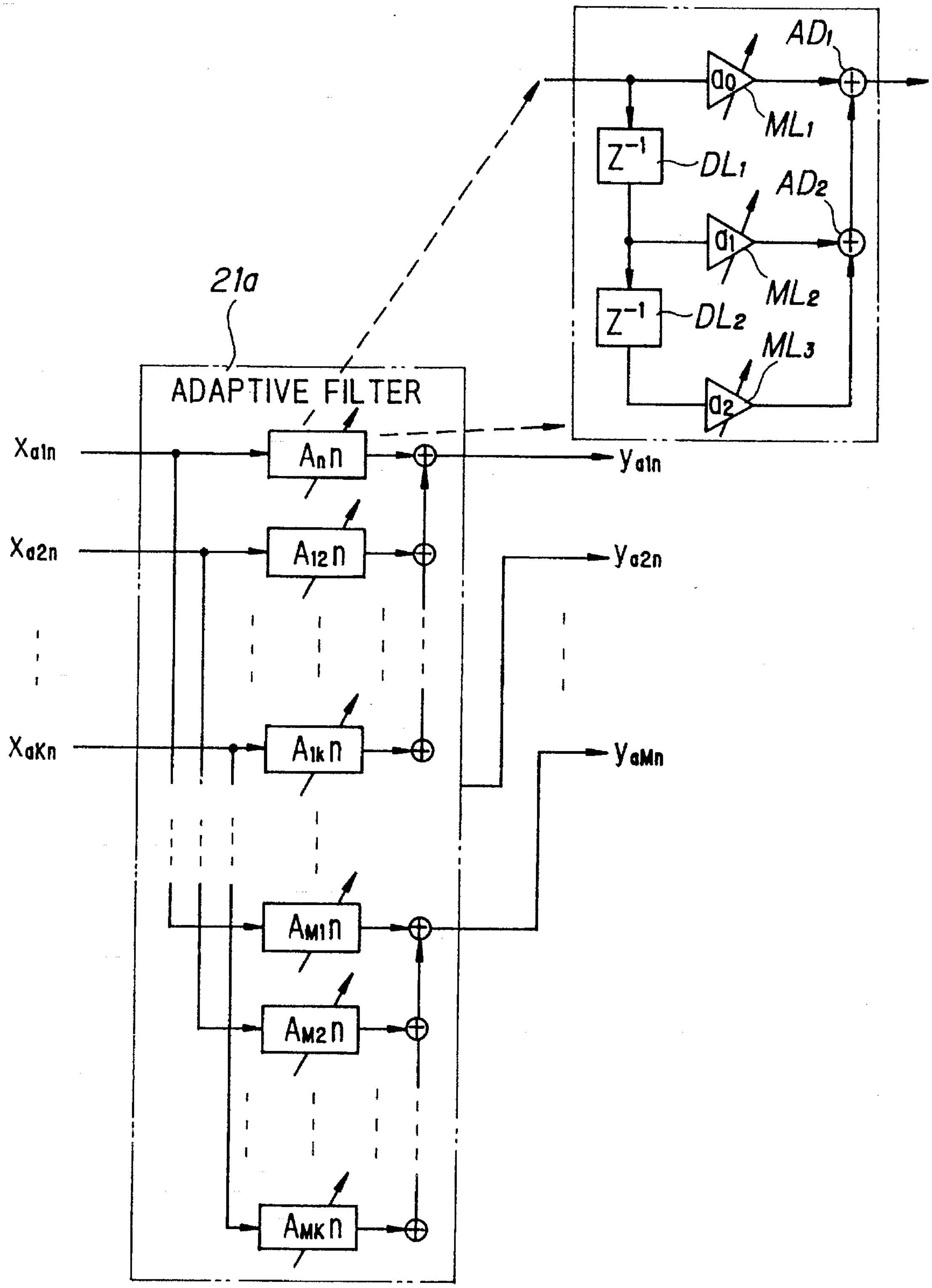
FIG. 16 (PRIOR ART)
FIG. 16 is a block diagram of an adaptive filter.
Figure 17:
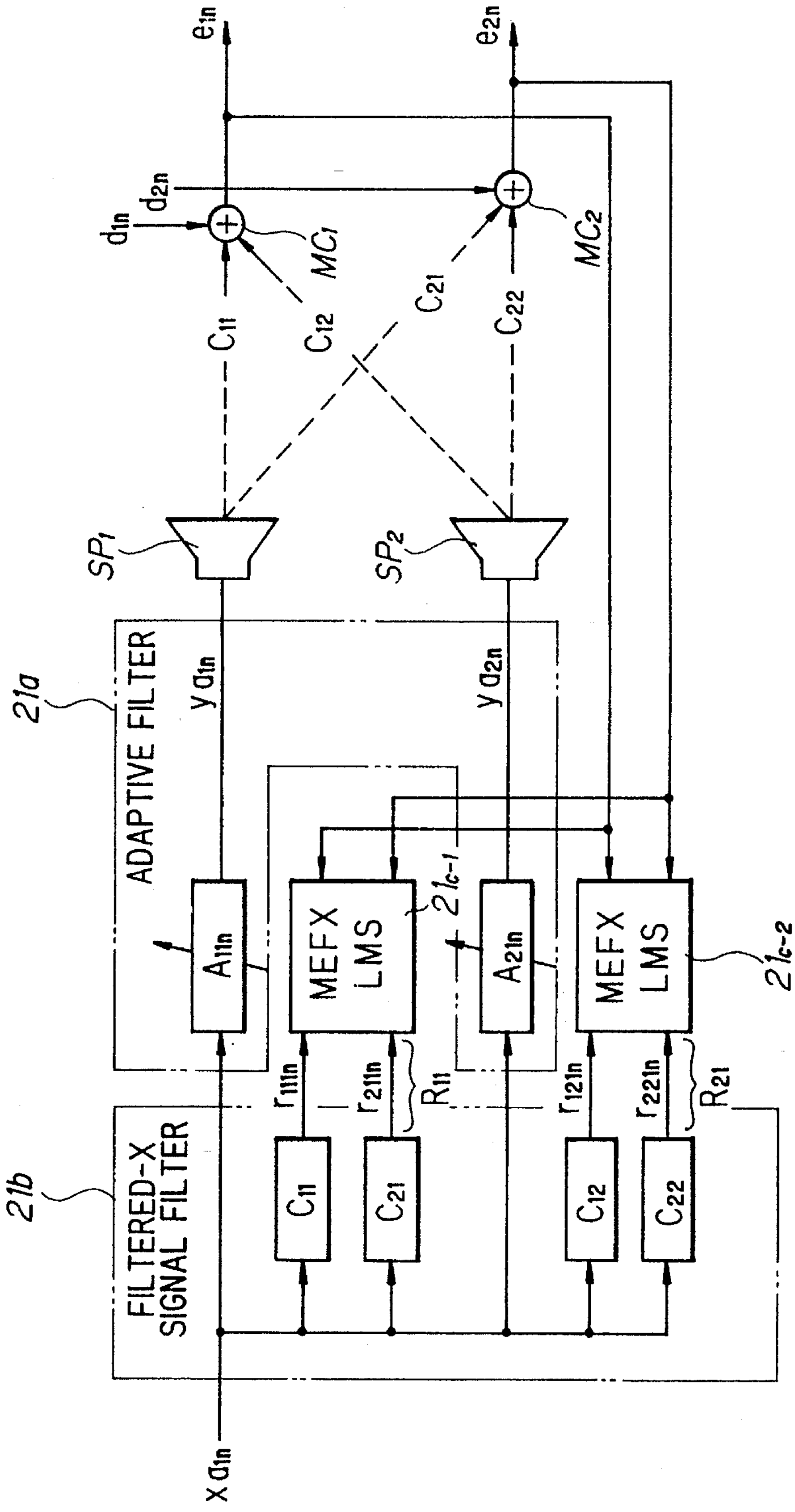
FIG. 17 (PRIOR ART)
FIG. 17 is a block diagram showing a prior-art noise-canceling apparatus for a case having one noise source, two speakers and two observation points.
Figure 18:
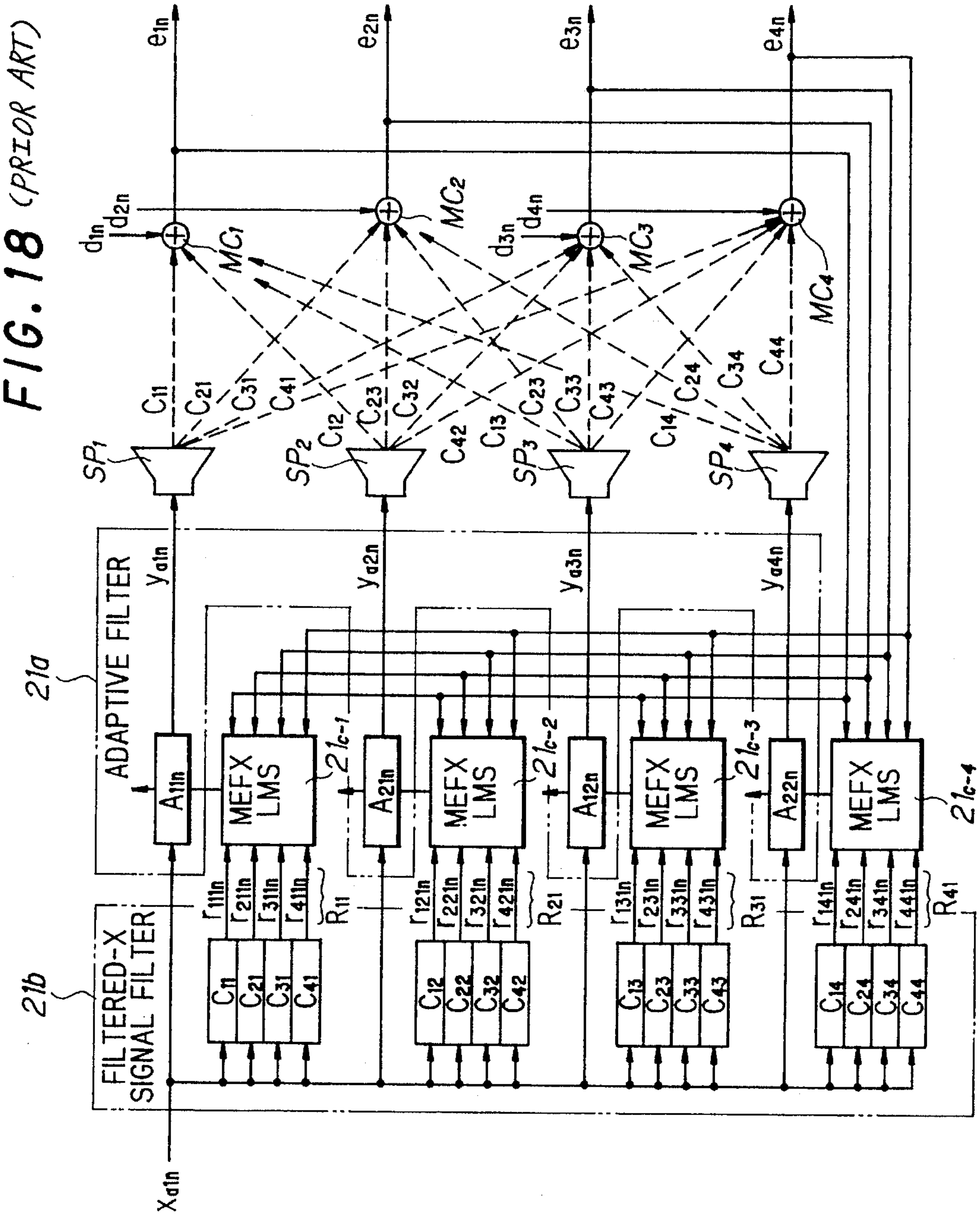
FIG. 18 (PRIOR ART)
FIG. 18 is a block diagram showing a prior-art noise-canceling apparatus for a case having one noise source, four speakers and four observation points.
Figure 19:
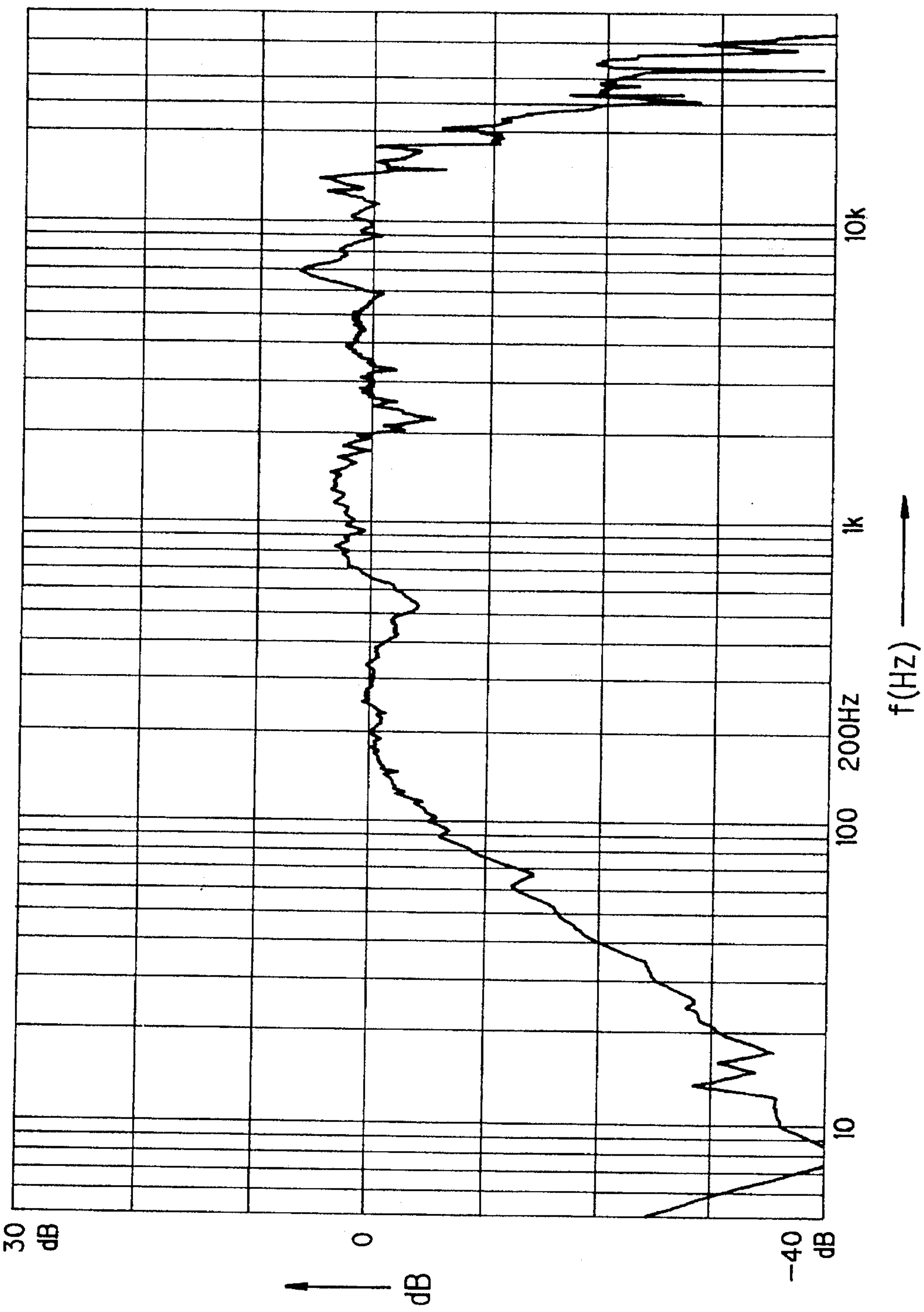
FIG. 19 is a characteristic diagram showing the frequency characteristic of a speaker.

FIG. 1 is a block diagram showing a noise-canceling apparatus according to a first embodiment of the present invention. Functional blocks identical with those of the prior-art apparatus shown in FIG. 9 are designated by like reference characters.

As shown in FIG. 1, the engine 11 which is the source of noise has its rotational speed R sensed by the rpm sensor 12. The output R of the sensor 12 is applied to the reference-signal generator 13, which generates the sinusoidal signal having a fixed amplitude and a frequency that conforms to the rotational speed R of the engine 11. The sinusoidal signal serves as the reference signal $x_n$. When the engine is a source of noise, the noise generated by rotation of the engine has periodicity (periodic noise) and the frequency of the noise is dependent upon the engine rotational speed. Accordingly, the reference-signal generator 13 stores the sinusoidal data in a ROM and generates the reference signal $x_n$ by reading out and delivering this data as necessary.

The reference signal $x_n$ generated by the reference-signal generator 13 is applied to the noise-canceling controller 14 as an input. Also fed into the controller 14 is the error signal en, which is a composite-sound signal that is a synthesis of the noise $S_n$ and the noise-canceling sound $S_c$ at the noise-canceling position (the observation point, such as a point in the vicinity of the ears of the driver) within the passenger compartment. The noise-canceling controller 14 outputs a noise-canceling signal $N_c$ by executing adaptive signal processing so as to minimize the error signal $e_n$. The power amplifier 15 amplifies the noise-canceling signal $N_c$ and applies the amplified signal to the canceling speaker (canceling-sound generating source) 16, which emits the noise-canceling sound $S_c$. The error microphone 17 is disposed at the noise-canceling point (observation point) so as to detect the aforesaid composite-sound signal, which is a synthesis of the noise $S_n$ and the noise-canceling sound $S_c$, and output the composite-sound signal as the error signal $e_n$. Numeral 18 denotes the canceling-sound propagation system (secondary-sound propagation system) in which the canceling sound is propagated from the speaker to the noise-canceling point.

In order to simplify the description, FIG. 1 illustrates an arrangement having one noise source, one speaker and one error microphone. However, the present invention is not limited to this arrangement but can be applied also to an arrangement in which a plurality of noise sources, a plurality of speakers and a plurality of microphones are provided.

Noise-canceling controller

The noise-canceling controller 14 includes the adaptive signal processor **14*a*, the adaptive filter 14*b* constructed as a digital filter, the DA converter 14*c* for converting the output of the adaptive filter 14*b* into the analog noise-canceling signal $N_c$, the filter 14*d* for producing the filtered-X signal used in adaptive signal processing, and a frequency-characteristic correcting unit 14*e***.

Figure 2:
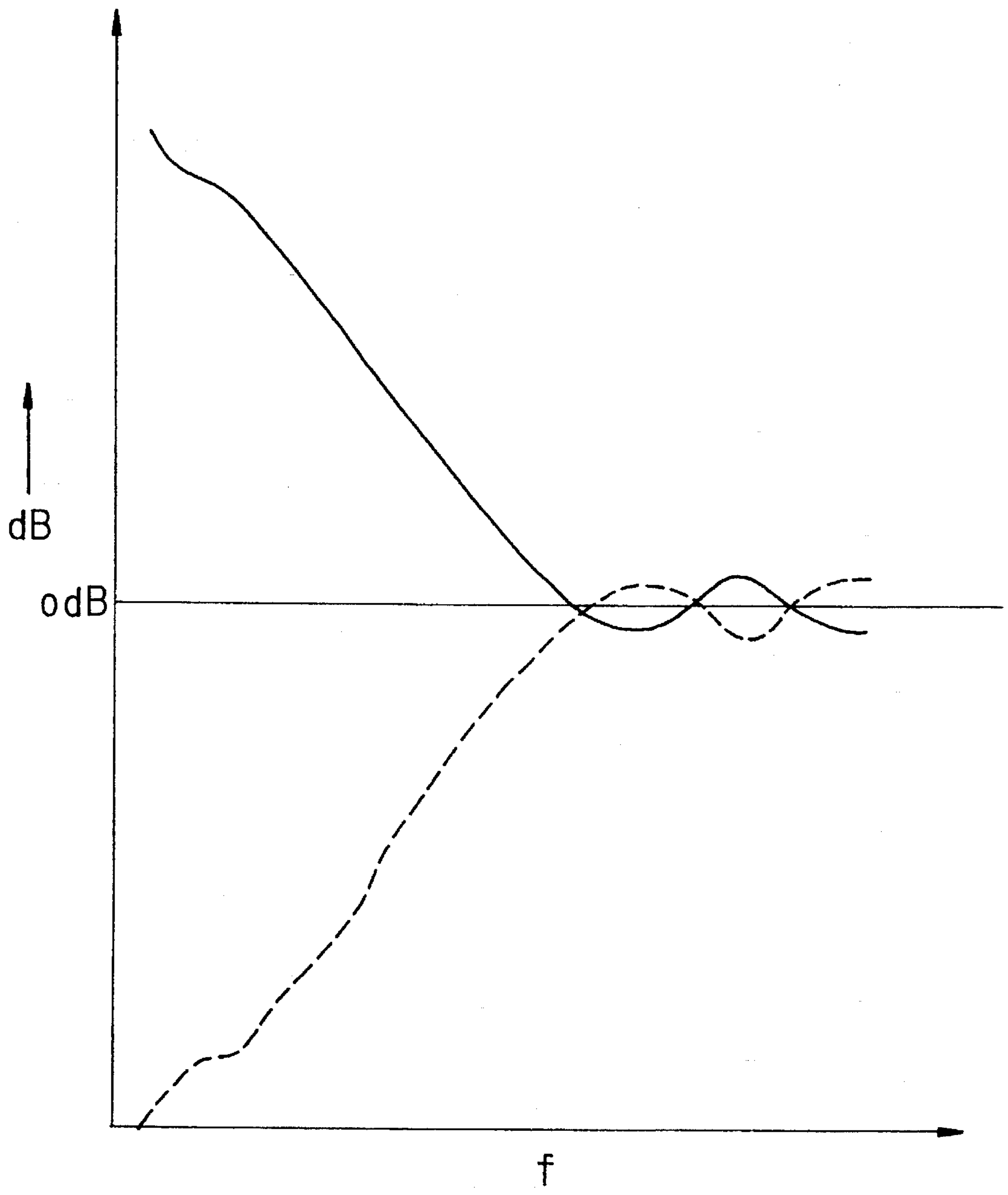
FIG. 2 is a characteristic diagram for describing the frequency characteristic of a frequency-characteristic correcting unit.

The frequency-characteristic correcting unit **14*e* has a frequency characteristic that is approximately symmetrical with respect to the frequency characteristic of the secondary-sound propagation system (which includes the speaker) 18 about a 0 dB line. The reference signal $x_n$ is applied to the correcting unit 14*e* as an input signal. FIG. 2 is a characteristic diagram showing the frequency characteristic of the frequency-characteristic correcting unit 14*e*. The dashed line indicates the frequency characteristic of the secondary-sound propagation system 18, and the solid line indicates the frequency characteristic of the frequency-characteristic correcting unit 14*e***.

Figure 3:
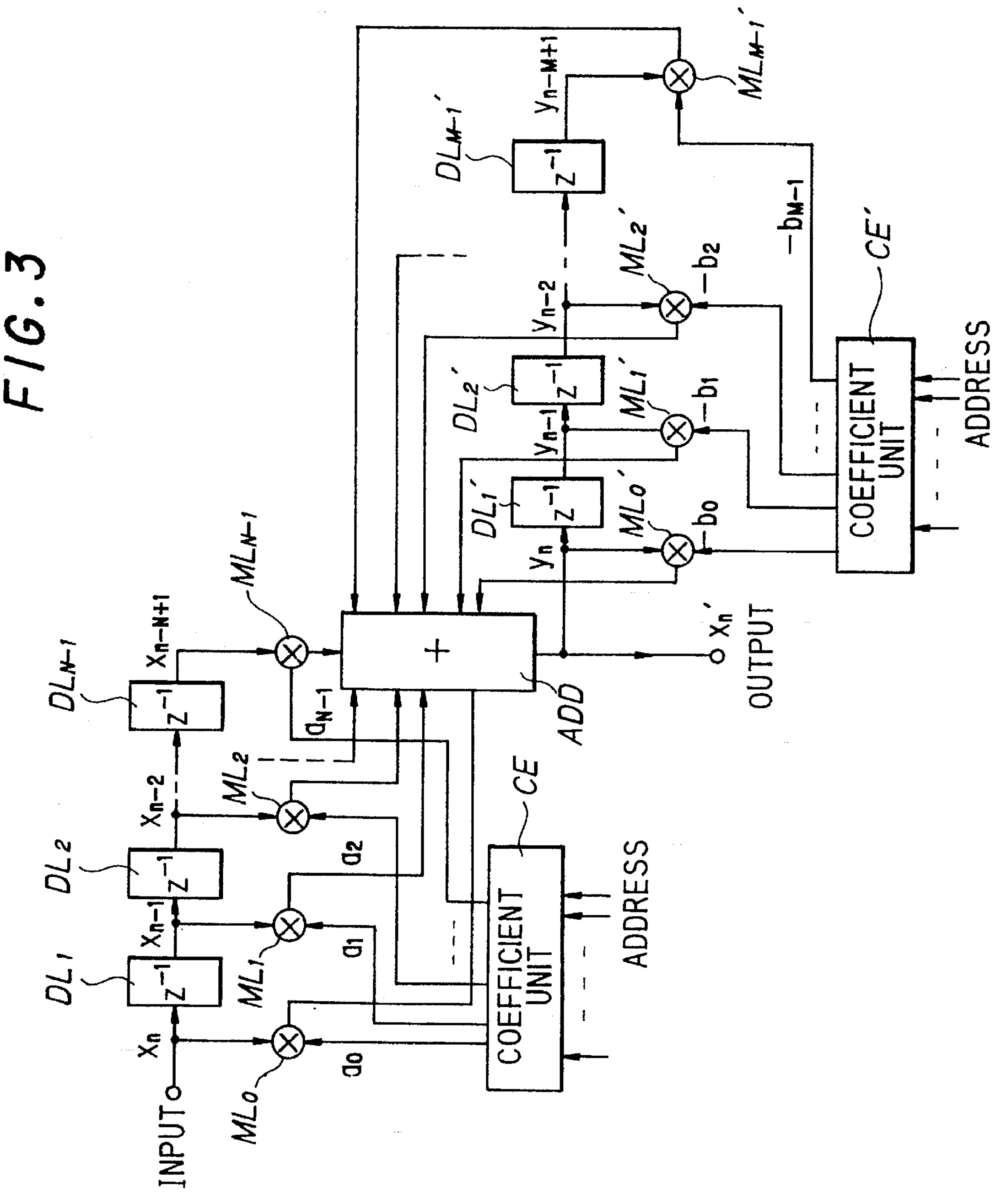
FIG. 3 is an explanatory view for a case in which the frequency-characteristic correcting unit is constituted by an IIR-type digital filter.

FIG. 3 shows an example in which the frequency-characteristic correcting unit **14*e* is constituted by an IIR-type digital filter. The correcting unit 14*e* includes delay elements DLi (i=1, 2, . . . , N−1) for successively delaying the input signal by one sampling period, a coefficient unit CE for storing coefficients $a_0$, $a_1$, $a_2$ . . . , multipliers MLi (i=0, 1, 2, . . . , N−1) for multiplying delay-element outputs $x_n$, $x_{n-1}$, $x_{n-2}$ . . . by the coefficients $a_0$, $a_1$, $a_2$ . . . , respectively, delay elements DLi' (i=1, 2, . . . , N−1) for successively delaying the output signal by one sampling period, a coefficient unit CE' for storing coefficients $b_0$, $b_1$, $b_2$ . . . , multipliers MLi' (i=0, 1, 2, . . . , N−1) for multiplying delay-element outputs $y_n$, $y_{n-1}$, $y_{n-2}$ . . . by the coefficients $b_0$, $b_1$, $b_2$ . . . , respectively, and an adder ADD for adding the outputs of all of the multipliers and producing a signal $y_n$ indicative of the sum. Thus, the frequency-characteristic correcting unit 14*e*** outputs a reference signal $x_n'$ (=$y_n$) by performing an operation in accordance with the following equation:

$$x_n' = \Sigma a_i \cdot x_{n-i} - \Sigma b_j \cdot y_{n-j} \ (i=0, 1, 2, \ldots, N-1; j=1, 2, \ldots M).$$

By adopting appropriate values for the coefficients $a_i$, $b_j$, it is possible to set a frequency characteristic that is approximately symmetrical with respect to the frequency characteristic of the secondary-sound propagation system 18 about a 0 dB line.

The filter **14*d* for producing a filtered-X signal is constructed based upon the transfer function of the secondary-sound propagation system. The input signal thereto is the reference signal $x_n'$ outputted by the frequency-characteristic correcting unit 14*e*. The error signal $e_n$ at the noise-canceling point and the filtered-X signal $r_n$, which is produced by the filter 14*d*, enter the adaptive signal processor 14*a*, which decides the coefficients of the adaptive filter 14*b* by using these two signals to execute adaptive signal processing in accordance with Equation (1) in such a manner that the noise at the noise-canceling point is canceled out. More specifically, the adaptive signal processor 14*a* decides the coefficients of the adaptive filter 14*b* in accordance with the well-known filtered-X LMS algorithm so as to minimize the error signal $e_n$ that has entered from the error microphone 17. In accordance with the coefficients decided by the adaptive signal processor 14*a*, the adaptive filter 14*b*** subjects the reference signal $x_n'$ to digital filtering processing so that the noise-canceling signal $N_c$ will be produced.

Overall operation

When the engine 11 rotates, the rotational speed R thereof is sensed by the rpm sensor 12 and the reference-signal generator 13 generates the reference signal $x_n$ that conforms to the engine rotational speed R. This signal enters the noise-canceling controller 14. At this time the periodic engine sound (periodic noise) generated by the engine 11 reaches the noise-canceling point upon propagating through space having a noise propagating system (primary-noise propagating system) that exhibits a prescribed transfer function. This sound is the noise $S_n$.

The error microphone 17 detects the composite sound that is the combination of the noise $S_n$ and canceling sound $S_c$ at the noise-canceling point and applies the resultant sound signal (the error signal) $e_n$ to the adaptive signal processor 14*a*.

In concurrence with the foregoing operation, the frequency-characteristic correcting unit 14*e* impresses a frequency characteristic, which is the reverse of that of the secondary-sound propagation system 18, upon the reference signal $x_n$ and applies the resulting signal $x_n'$ to the adaptive filter 14*b* and filtered-X signal producing filter 14*d*. The filter 14*d* superimposes the transfer function of the secondary-sound propagation system 18 upon the reference signal $x_n'$ outputted by the frequency-characteristic correcting unit 14*e*, thereby generating the filtered-X signal $r_n$ used in adaptive signal processing. This signal is fed into the adaptive signal processor 14*a*.

The adaptive signal processor 14*a* decides the coefficients of the adaptive filter 14*b* by performing adaptive signal processing in accordance with Equation (1) using the composite-sound signal (error signal) $e_n$ and the filtered-X signal $r_n$, which is outputted by the filter 14*d*.

On the basis of the coefficients decided by the adaptive signal processor 14*a*, the adaptive filter 14*b* produces the noise-canceling signal $y_n$ by applying digital filtering processing to the reference signal $x_n'$ that enters from the frequency-characteristic correcting unit 14*e*. The DA converter 14*c* subjects the adaptive filter output to a DA conversion to generate the analog noise-canceling signal $N_c$, which enters the speaker 16 via the power amplifier 15. As a result, the speaker outputs a noise-canceling sound that arrives at the noise-canceling point via the secondary-sound propagation system 18 to cancel out the noise $S_n$. The foregoing operation is repeated to cancel out the noise in a rapid manner.

In the foregoing, the frequency characteristic of the frequency-characteristic correcting unit 14*e* is symmetrical to the frequency characteristic of the secondary-sound propagation system about the 0 dB level. The overall frequency characteristic therefore is flat. Accordingly, the second term $\mu R_{ij} e_n$ on the right side of Equation (1) may be written as follows if we let C represent the characteristic of the secondary-sound propagation system and C' the characteristic of the frequency-characteristic correcting unit 14*e*:

$$\begin{aligned} \mu R_{ij} e_n &= \mu C C' x_{ajn} e_n \\ &= \mu x_{ajn} e_n \end{aligned} \quad (4)$$

Consequently, the adaptive signal processor 14*a* is capable of executing adaptive signal processing just as if the secondary-sound propagation system possessed a frequency characteristic having a constant gain. The result is that the coefficient convergence characteristic of the adaptive algorithm can be advanced to improve follow-up with respect to any fluctuation in noise, thereby making it possible to manifest a satisfactory noise-canceling effect.

Figure 4A:
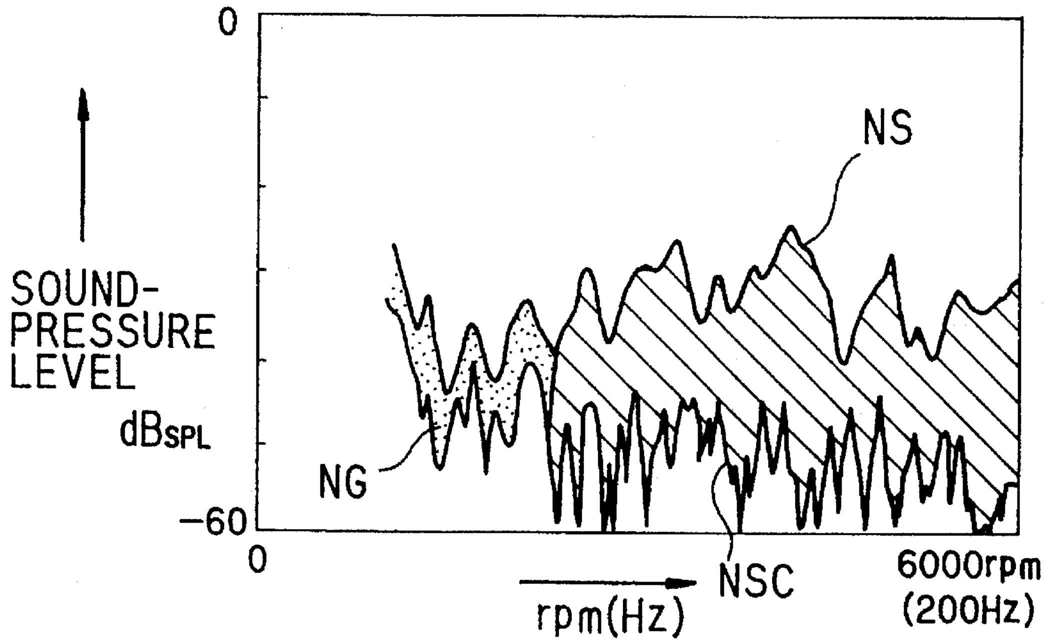
FIG. 4A is an explanatory view of a noise-canceling effect according to a prior-art apparatus.
Figure 4B:
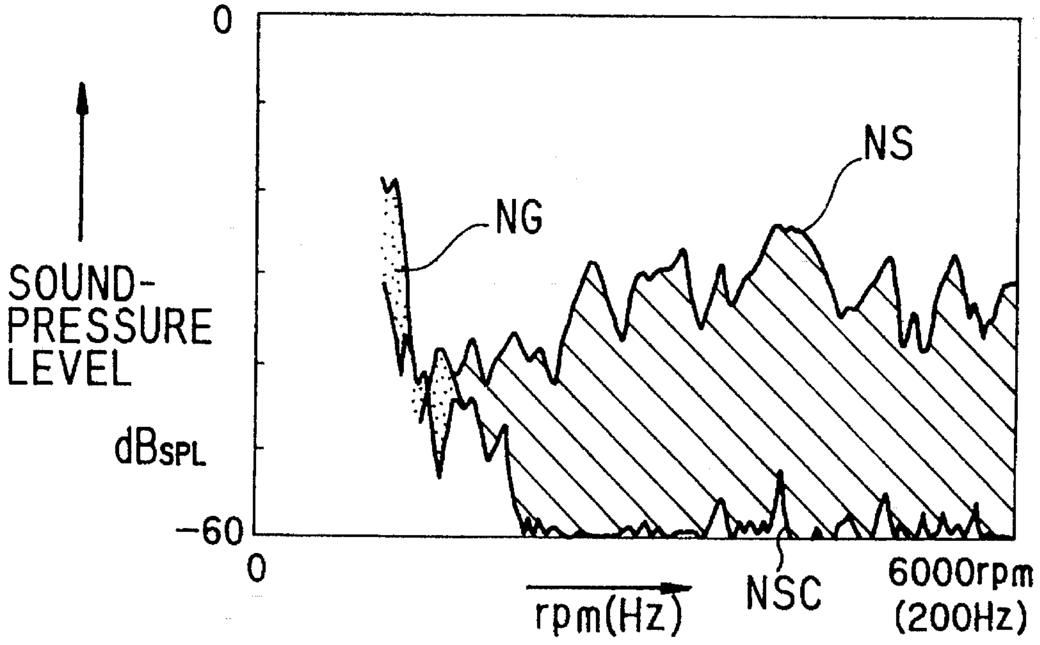
FIG. 4B is an explanatory view of a noise-canceling effect according to a first embodiment of the invention.

FIG. 4 is useful in describing the noise-canceling effect of the present invention. FIG. 4A is an explanatory view of the noise-canceling effect obtained with the prior-art apparatus, in which the frequency-characteristic correcting unit 14*e* is not included, and FIG. 4B is an explanatory view of the noise-canceling effect according to the apparatus of the present invention having the frequency-characteristic correcting unit 14*e*. In FIGS. 4A and 4B, engine rotational speed in rpm (frequency of noise in Hz) is plotted along the horizontal axis, and noise level ($dB_{SpL}$) is plotted along the vertical axis. Further, NS represents noise sound-pressure level at an observation point in a case where noise is not canceled, and NSC represents noise sound-pressure level at an observation point in a case where noise is canceled. Noise-canceling effects indicated by the hatching in each of FIGS. 4A and 4B are obtained. A comparison of FIGS. 4A and 4B reveals that the noise-canceling effect provided by the noise-canceling apparatus of the present invention is superior to that provided by the conventional apparatus. It should be noted that NG in FIGS. 4A and 4B indicates an augmented area in which noise is amplified.

The foregoing relates to a case in which the frequency-characteristic correcting unit is digitally constructed. However, the correcting unit can be constructed in analog fashion using a graphic equalizer or the like.

(b) Second embodiment of the invention

Overall configuration

Figure 5:
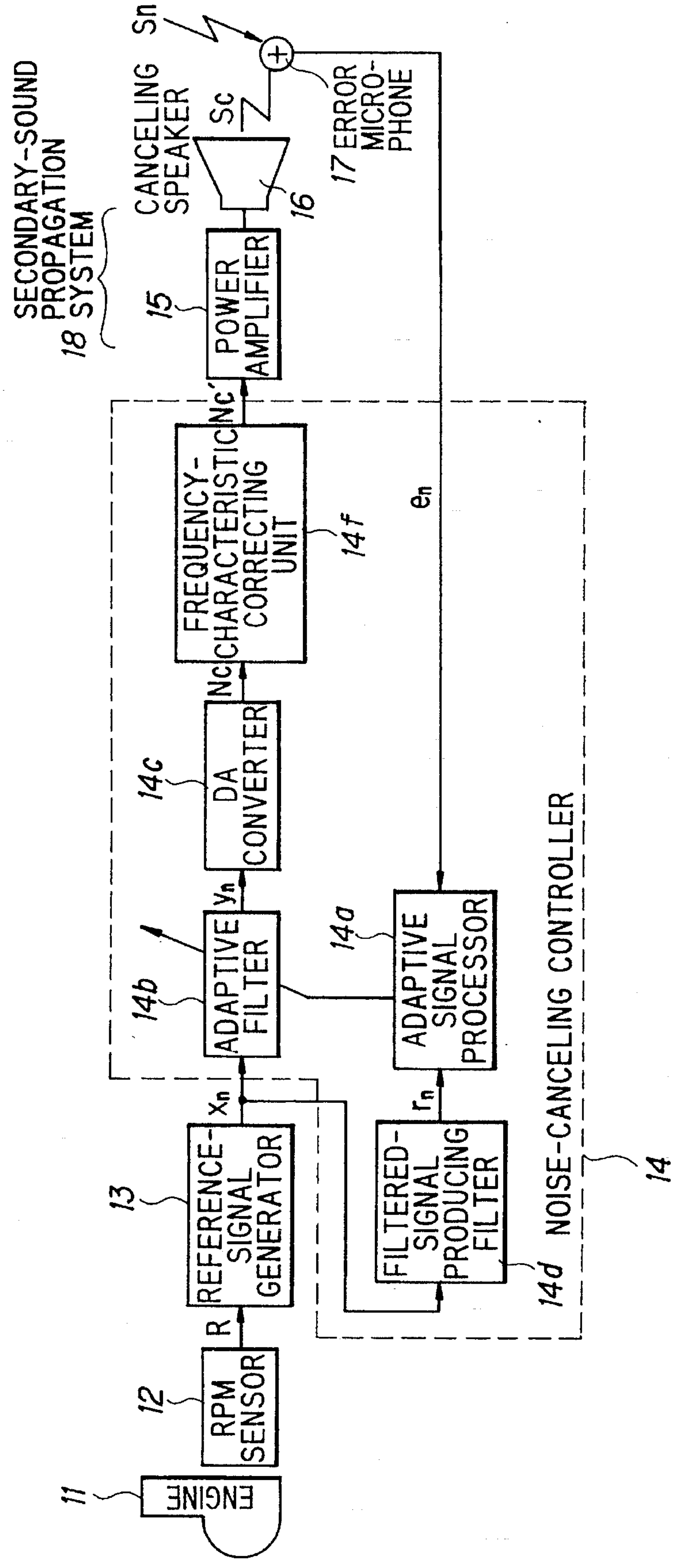
FIG. 5 is a block diagram showing a second embodiment of the present invention.

FIG. 5 is a block diagram showing a noise-canceling apparatus according to a second embodiment of the present invention. Functional blocks identical with those of the first embodiment shown in FIG. 1 are designated by like reference characters.

As shown in FIG. 5, the engine 11 which is the source of noise has its rotational speed R sensed by the rpm sensor 12. The output R of the sensor 12 is applied to the reference-signal generator 13, which generates the sinusoidal signal having a fixed amplitude and a frequency that conforms to the rotational speed R of the engine 11. The sinusoidal signal serves as the reference signal $x_n$. The reference signal $x_n$ generated by the reference-signal generator 13 is applied to the noise-canceling controller 14 as an input. Also fed into the controller 14 is the error signal $e_n$, which is a composite-sound signal that is a synthesis of the noise $S_n$ and the noise-canceling sound $S_c$ at the noise-canceling position within the passenger compartment. The noise-canceling controller 14 outputs a noise-canceling signal $N_c'$ by executing adaptive signal processing so as to minimize the error signal $e_n$. The power amplifier 15 amplifies the noise-canceling signal $N_c'$ and applies the amplified signal to the canceling speaker (canceling-sound generating source) 16, which emits the noise-canceling sound $S_c$. The error microphone 17 is disposed at the noise-canceling point (observation point) so as to detect the aforesaid composite-sound signal, which is a synthesis of the noise $S_n$ and the noise-canceling sound $S_c$, and output the composite-sound signal as the error signal $e_n$. The canceling-sound propagation system (secondary-sound propagation system) 18 is that in which the canceling sound is propagated from the speaker to the noise-canceling point.

Noise-canceling controller

Figure 6:
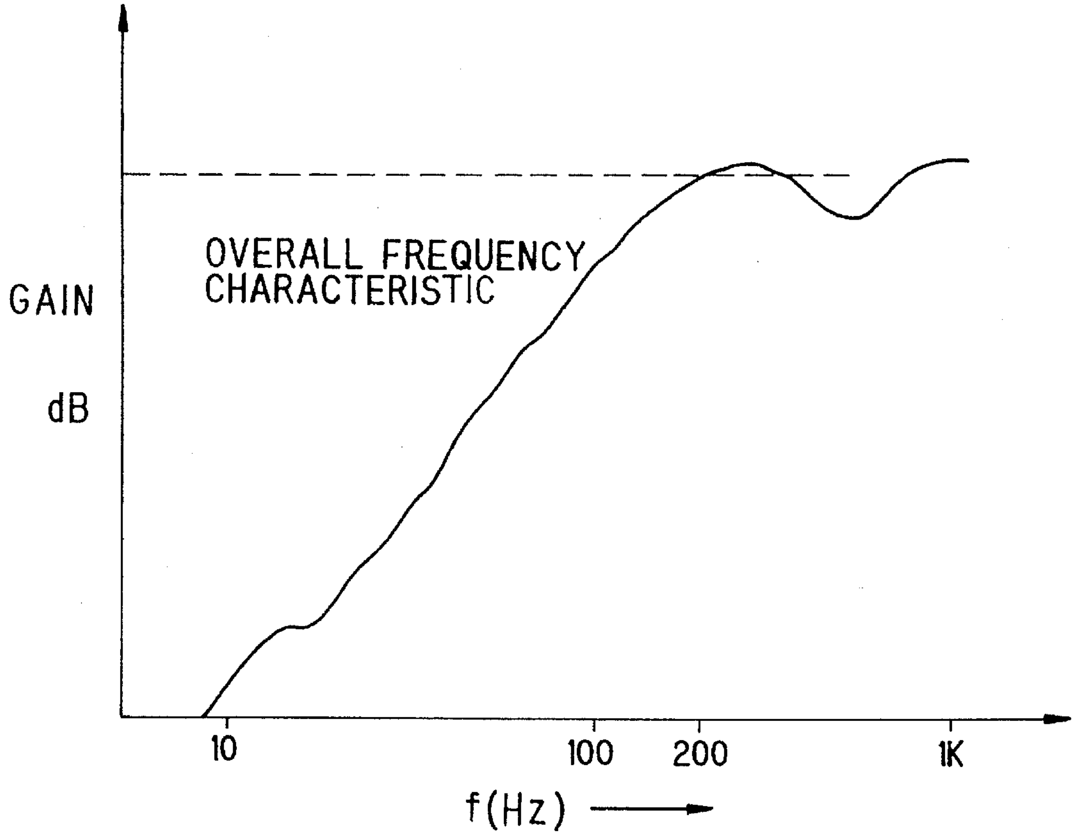
FIG. 6 is a characteristic diagram for describing the frequency characteristic of a frequency-characteristic correcting unit.

The noise-canceling controller 14 includes the adaptive signal processor 14*a*, the adaptive filter 14*b* constructed as a digital filter, the DA converter 14*c* for converting the output $y_n$ of the adaptive filter 14*b* into the analog noise-canceling signal $N_c$, the filter 14*d* for producing the filtered-X signal used in adaptive signal processing, and a frequency-characteristic correcting unit 14*f*. The frequency-characteristic correcting unit 14*f* has a frequency characteristic that is set in such a manner that the overall frequency characteristic in combination with the frequency characteristic of the canceling-sound propagation system 18 is substantially flat. FIG. 6 is a diagram for describing the characteristic correction performed by the frequency-characteristic correcting unit 14*f*. The solid line indicates the frequency characteristic of the secondary-sound propagation system 18, and the dashed line indicates the ideal overall frequency characteristic that results after the insertion of the frequency-characteristic correcting unit 14*f*.

Figure 7:
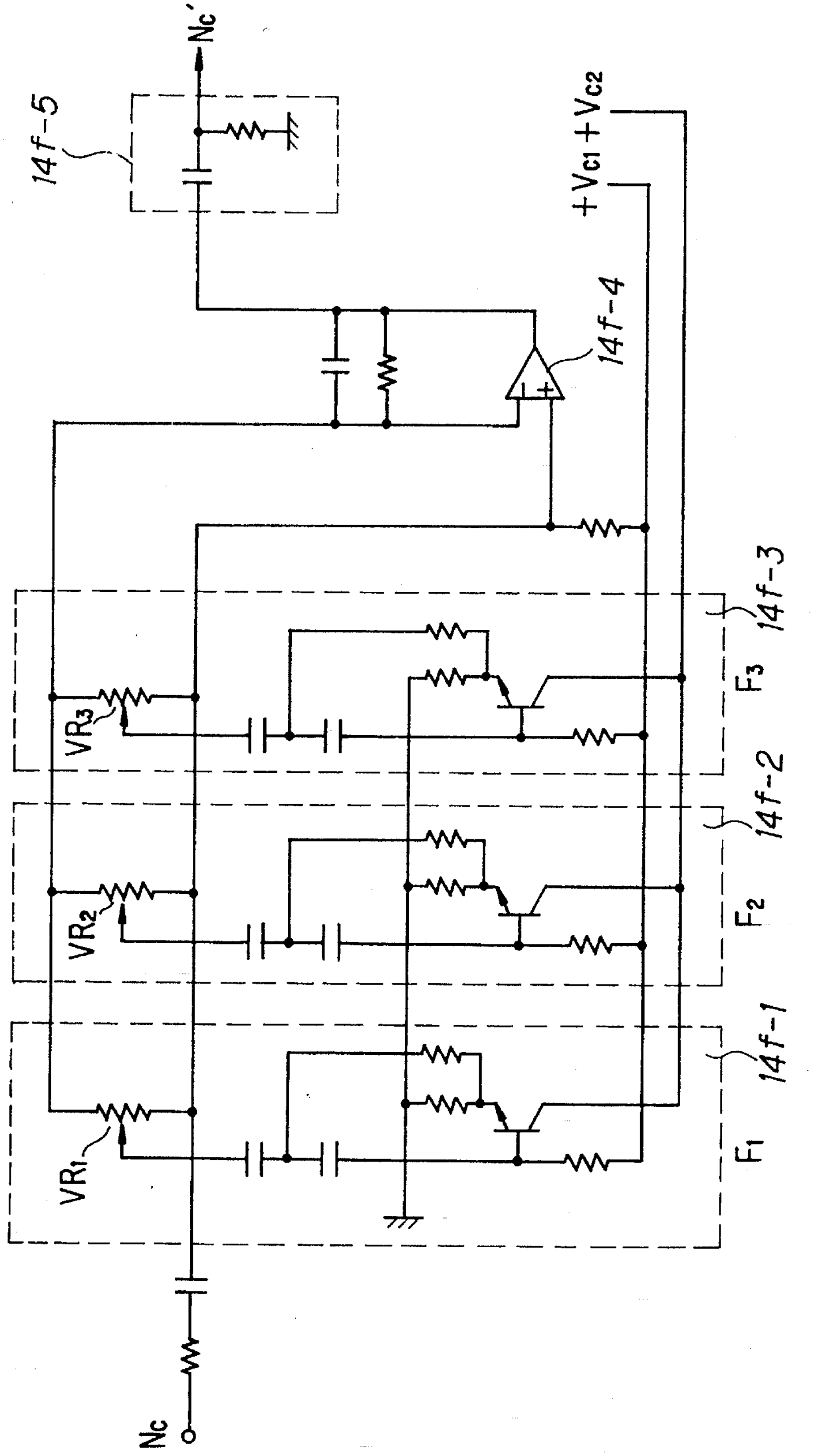
FIG. 7 is an explanatory view for a case in which the frequency-characteristic correcting unit is constituted by an equalizer.

FIG. 7 is a diagram useful in describing a case in which the frequency-characteristic correcting unit 14*f* is constituted by a graphic equalizer. Here the frequency characteristics in three bands $F_1$, $F_2$, $F_3$ are controlled independently. As shown in FIG. 7, the correcting unit includes a characteristic controller 14*f*-1 for controlling the characteristic of band $F_1$, a characteristic controller 14*f*-2 for controlling the characteristic of band $F_2$, a characteristic controller 14*f*-3 for controlling the characteristic of band $F_3$, a bridge amplifier 14*f*-4, an output circuit 14*f*-5, and variable resistors $VR_1$~$VR_3$ for setting the gain or attenuation quantities of each of the bands $F_1$~$F_3$, respectively. The noise-canceling signal $N_c$ outputted by the DA converter 14*c* enters the + terminal of the bridge amplifier 14*f*-4 and one end of each of the variable resistors $VR_1$~$VR_3$ of the respective characteristic controllers 14*f*-1~14*f*-3. The other ends of the variable resistors $VR_1$~$VR_3$ are tied together and connected to the − terminal of the bridge amplifier 14*f*-4. By virtue of this arrangement, the frequency characteristics of each of the bands $F_1$~$F_3$ are controlled based upon the set values of the variable resistors $VR_1$~$VR_3$, as a result of which a prescribed overall frequency characteristic is obtained. Though a case in which the frequency characteristics of only three bands are controlled has been described for the sake of simplifying the explanation, it goes without saying that the frequency-characteristic correcting unit can be constructed in similar fashion for controlling the frequencies of four or more bands.

The filtered-X signal producing filter 14*d* is constructed using an overall transfer function from the frequency-characteristic correcting unit 14*e* to the noise-canceling point. Since the frequency characteristic is flat, the filtered-X signal producing filter 14*d* can be constructed solely of delay elements having a fixed gain.

The error signal $e_n$ at the noise-canceling point and the filtered-X signal $r_n$, which is produced by the filter 14*d*, enter the adaptive signal processor 14*a*, which decides the coefficients of the adaptive filter 14*b* by using these two signals to execute adaptive signal processing in accordance with Equation (1) in such a manner that the noise at the noise-canceling point is canceled out. More specifically, the adaptive signal processor 14*a* decides the coefficients of the adaptive filter 14*b* in accordance with the filtered-X LMS algorithm so as to minimize the error signal $e_n$ that has entered from the error microphone 17. In accordance with the coefficients decided by the adaptive signal processor 14*a*, the adaptive filter 14*b* subjects the reference signal $x_n$ to digital filtering processing so that the noise-canceling signal $y_n$ will be produced.

Overall operation

When the engine 11 rotates, the rotational speed R thereof is sensed by the rpm sensor 12 and the reference-signal generator 13 generates the reference signal $x_n$ that conforms to the engine rotational speed R. This signal enters the noise-canceling controller 14. At this time the periodic engine sound (periodic noise) generated by the engine 11 reaches the noise-canceling point upon propagating through space having a noise propagating system (primary-noise propagating system) that exhibits a prescribed transfer function.

The error microphone 17 detects the composite sound that is the combination of the noise $S_n$ and canceling sound $S_c$ at the noise-canceling point and applies the resultant sound signal (the error signal) $e_n$ to the adaptive signal processor 14*a*.

In concurrence with the foregoing operation, the filtered-X signal producing filter 14*d* receives the reference signal $x_n$ as an input, generates the filtered-X signal $r_n$ used in the filtered-X LMS algorithm processing and applies this signal to the adaptive signal processor 14*a*.

The adaptive signal processor 14*a* decides the coefficients of the adaptive filter 14*b* by performing adaptive signal processing in accordance with Equation (1) using the error signal $e_n$ and the filtered-X signal $r_n$, which is outputted by the filter 14*d*.

In accordance with the coefficients decided by the adaptive signal processor 14*a*, the adaptive filter 14*b* produces the noise-canceling signal $y_n$ by applying digital filtering processing to the reference signal $x_n$. The DA converter 14*c* subjects the adaptive filter output $y_n$ to a DA conversion and inputs the resulting analog quantity to the frequency-characteristic correcting unit 14*e*. The latter impresses the preset frequency characteristic upon the noise-canceling signal inputted thereto and applies the resulting signal to the speaker 16 via the power amplifier 15. As a result, the speaker outputs a noise-canceling sound that arrives at the noise-canceling point via the secondary-sound propagation system 18 to cancel out the noise. The foregoing operation is repeated to cancel out the noise in a rapid manner.

In the foregoing, the overall frequency characteristic of the frequency-characteristic correcting unit 14*e* and secondary-sound propagation system 18 is substantially flat, and therefore the adaptive signal processor 14*a* need only perform noise-canceling control in a system having a fixed gain. In other words, the adaptive signal processor 14*a* need only perform noise-canceling control in which the gains of the filtered-X signal producing filters $$(C_{ii}, C_{2i}, C_{3i}, \ldots, C_{Li})$$

in Equation (2) are fixed. The result is that the coefficient convergence characteristic of the adaptive algorithm can be advanced to improve follow-up with respect to any fluctuation in noise, thereby making it possible to manifest a satisfactory noise-canceling effect.

The second embodiment provides a noise-canceling effect similar to that of the first embodiment. That is, the noise sound-pressure level is as indicated at NSC in FIG. 4B in the second embodiment as well, and the noise-canceling effect obtained is as indicated by the hatched area.

(c) Third embodiment of the invention

Overall configuration

Figure 8:
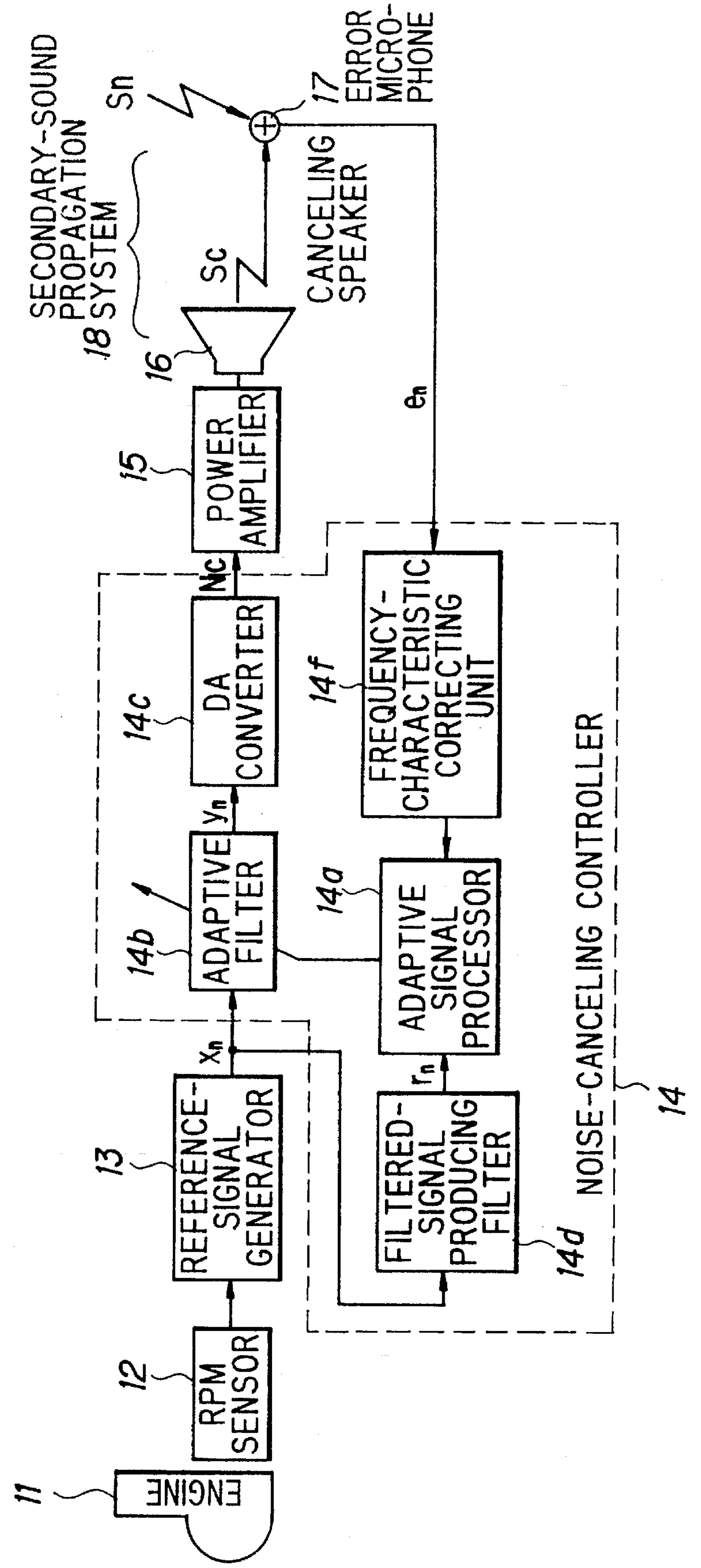
FIG. 8 is a block diagram showing a third embodiment of the present invention.

FIG. 8 is a block diagram showing a noise-canceling apparatus according to a third embodiment of the present invention. Functional blocks identical with those of the second embodiment are designated by like reference characters.

The third embodiment differs from the second embodiment in the location of the frequency-characteristic correcting unit 14*f*. In the second embodiment, the frequency-characteristic correcting unit 14*f* is provided on the input side of the speaker 16 (the output signal of the DA converter 14*c*). In the third embodiment, the frequency-characteristic correcting unit 14*f* is provided in the feedback path that feeds back the error signal $e_n$ to the adaptive signal processor 14*a*. By adopting this arrangement, effects identical with those of the first and second embodiments are obtained. That is, since the overall frequency characteristic of the frequency-characteristic correcting unit 14*f* and secondary-sound propagation system 18 is flat, the second term $\mu R_{ij}e_n$ on the right side of Equation (1) may be written as follows if we let C represent the characteristic of the secondary-sound propagation system and C' the characteristic of the frequency-characteristic correcting unit 14*f*:

$$\mu R_{ij}e_n = \mu Cx_{ajn}e_nC' = \mu x_{ajn}e_n \quad (4)'$$

Consequently, the adaptive signal processor 14*a* is capable of executing adaptive signal processing just as if the secondary-sound propagation system possessed a frequency characteristic having a constant gain. The result is that the coefficient convergence characteristic of the adaptive algorithm can be advanced to improve follow-up with respect to any fluctuation in noise, thereby making it possible to manifest a satisfactory noise-canceling effect.

In the second and third embodiments, the frequency-characteristic correcting unit is described as being composed of a graphic equalizer. However, the correcting unit can be constructed using an IIR-type digital filter.

In accordance with the present invention as described above, a frequency-characteristic correcting unit is provided on the input side of an adaptive filter in a noise-canceling controller and the frequency characteristic of the correcting unit is set so as to be approximately symmetrical to that of the canceling-sound propagation system about a 0 dB line. As a result, the overall frequency characteristic of the frequency-characteristic correcting unit and canceling-sound propagation system becomes substantially flat and the coefficient convergence characteristic of the adaptive filter based upon adaptive signal processing is improved. This makes it possible to achieve a satisfactory noise-canceling effect.

Further, in accordance with the present invention, a frequency-characteristic correcting unit is provided either on the input side of a canceling-noise generating source or in a feedback section for feeding back an error signal to a noise-canceling controller. The overall frequency characteristic of the frequency-characteristic correcting unit and canceling-sound propagation system is made substantially flat (i.e., gain is made constant) and the coefficient convergence of the adaptive filter that relies upon adaptive signal processing is improved. This makes it possible to achieve a satisfactory noise-canceling effect.

As many apparently widely different embodiments of the present invention can be made without departing from the spirit and scope thereof, it is to be understood that the invention is not limited to the specific embodiments thereof except as defined in the appended claims.

What is claimed is:

1. A noise-canceling apparatus comprising:

a canceling-sound generating source for outputting a canceling sound in order to cancel noise at a noise-canceling point;

a sensor for sensing a composite sound that is a composite of the noise and canceling sound at the noise-canceling point; and a noise-canceling controller, to which a composite-sound signal indicative of the composite sound at the noise-canceling point and a reference signal conforming to noise generated by a noise source are inputted, for updating coefficients of an adaptive filter using the composite-sound signal and the reference signal so as to cancel the noise at the noise-canceling point by adaptive signal processing, inputting the reference signal to said adaptive filter to generate a noise-canceling signal and inputting the noise-canceling signal to said canceling-sound generating source;

said noise-canceling apparatus further comprising a frequency-characteristic correcting unit provided on an input side of said adaptive filter in said noise-canceling controller and having a frequency characteristic that is substantially symmetrical, about a 0 dB line, with respect to a frequency characteristic of a canceling-sound propagation system from said canceling-sound generating source to said sensor;

said noise-canceling controller executing adaptive signal processing, with a signal obtained by inputting said reference signal to said frequency-characteristic correcting unit being used as a true reference signal.

2. The apparatus according to claim 1, wherein said canceling-sound generating source is a speaker and said canceling-sound propagation system includes said speaker.

3. A noise-canceling apparatus comprising:

a canceling-sound generating source for outputting a canceling sound in order to cancel noise at a noise-canceling point;

a sensor for sensing a composite sound that is a composite of the noise and canceling sound at the noise-canceling point; and a noise-canceling controller, to which a composite-sound signal indicative of the composite sound at the noise-canceling point and a reference signal conforming to noise generated by a noise source are inputted, for updating coefficients of an adaptive filter using the composite-sound signal and the reference signal so as to cancel the noise at the noise-canceling point by adaptive signal processing, inputting the reference signal to said adaptive filter to generate a noise-canceling signal, and inputting the noise-canceling signal to the canceling-sound generating source;

said noise-canceling apparatus further comprising a frequency-characteristic correcting unit provided between said adaptive filter and said canceling-sound generating source, an overall frequency characteristic of said frequency-characteristic correcting unit and a canceling-sound propagation system being made substantially flat.

4. The apparatus according to claim 3, wherein said canceling-sound generating source is a speaker and said canceling-sound propagation system includes said speaker.

* * * * *

UNITED STATES PATENT AND TRADEMARK OFFICE

CERTIFICATE OF CORRECTION

PATENT NO. : 5,524,057

DATED : June 4, 1996

INVENTOR(S) : Masaichi AKIHO, et al.

It is certified that error appears in the above-indentified patent and that said Letters Patent is hereby corrected as shown below: Item [56]

Title Page, References Cited, beneath the listing of U.S. PATENT DOCUMENTS, insert the following:

--FOREIGN PATENT DOCUMENTS

| | | |
|---|---|---|
| 0492680 | 1/1992 | European Patent Office |
| 0465174 | 8/1992 | European Patent Office |
| 0517525 | 9/1992 | European Patent Office--. |

Column 10, line 36, delete the paragraph indentation so that the line is flush with the left margin and is shown to continue the paragraph.

Column 12, line 1, delete "$dB_{SpL}$" and insert therefor --$dB_{SPL}$--.

Signed and Sealed this

Twenty-seventh Day of August, 1996

Attest:

BRUCE LEHMAN

*Attesting Officer* *Commissioner of Patents and Trademarks*